(12) United States Patent
Courtney et al.

(10) Patent No.: US 9,839,410 B2
(45) Date of Patent: *Dec. 12, 2017

(54) MEDICAL PROBE WITH FLUID ROTARY JOINT

(71) Applicant: CONAVI MEDICAL INC., Toronto (CA)

(72) Inventors: Brian Courtney, Toronto (CA); Amandeep Thind, North York (CA); Isaac Jourard, Toronto (CA)

(73) Assignee: CONAVI MEDICAL INC., Toronto, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/207,147

(22) Filed: Jul. 11, 2016

(65) Prior Publication Data
US 2017/0007203 A1  Jan. 12, 2017

Related U.S. Application Data

(63) Continuation of application No. 13/482,896, filed on May 29, 2012, now Pat. No. 9,387,305.
(Continued)

(51) Int. Cl.
*A61B 8/14* (2006.01)
*A61B 8/00* (2006.01)
(Continued)

(52) U.S. Cl.
CPC ............ *A61B 8/445* (2013.01); *A61B 1/0016* (2013.01); *A61B 1/0057* (2013.01); *A61B 1/00142* (2013.01); *A61B 1/015* (2013.01); *A61B 8/12* (2013.01); *A61B 17/320758* (2013.01); *A61M 25/0028* (2013.01); *A61M 25/0082* (2013.01); *A61M 25/0097* (2013.01); *A61M 25/10* (2013.01); *A61M 39/223* (2013.01); *A61M 39/225* (2013.01); *A61B 18/24* (2013.01); *A61B 2018/0212* (2013.01); *A61B 2090/3735* (2016.02); *A61B 2090/3784* (2016.02); *A61M 25/104* (2013.01); *A61M 2025/0019* (2013.01);
(Continued)

(58) Field of Classification Search
None
See application file for complete search history.

(56) References Cited

U.S. PATENT DOCUMENTS 5,624,392 A * 4/1997 Saab ..................... A61F 7/123
                                                      604/113

* cited by examiner

*Primary Examiner* — Joel F Brutus
(74) *Attorney, Agent, or Firm* — Hill & Schmacher

(57) ABSTRACT

A catheter is provided that includes an external sheath, a rotatable conduit housed within the external sheath, and a fluid rotary joint having a rotatable insert that places an inner lumen of the rotatable conduit in fluid communication with an external port under rotation of the rotatable conduit. The rotatable insert may include a channel structure including an external annular channel. The rotatable conduit is received within the channel structure such that the inner lumen is in fluid communication with the external port through the annular channel under rotation. The external sheath may define an outer lumen that may be in fluid communication with the inner lumen at a location remote from a proximal portion of the catheter, and the outer lumen may be in fluid communication with a secondary port. The rotatable conduit may be housed within a torque cable that is connected to the rotatable insert.

22 Claims, 18 Drawing Sheets

Related U.S. Application Data

(60) Provisional application No. 61/490,930, filed on May 27, 2011.

(51) Int. Cl.

| | | |
|---|---|---|
| *A61B 1/00* | (2006.01) | |
| *A61B 1/005* | (2006.01) | |
| *A61B 1/015* | (2006.01) | |
| *A61B 8/12* | (2006.01) | |
| *A61M 25/00* | (2006.01) | |
| *A61M 39/22* | (2006.01) | |
| *A61B 17/3207* | (2006.01) | |
| *A61M 25/10* | (2013.01) | |
| *A61B 18/24* | (2006.01) | |
| *A61B 18/02* | (2006.01) | |
| *A61M 39/10* | (2006.01) | |
| *A61N 7/00* | (2006.01) | |
| *A61B 90/00* | (2016.01) | |

(52) U.S. Cl.
CPC ............... *A61M 2025/0039* (2013.01); *A61M 2039/1077* (2013.01); *A61N 7/00* (2013.01)

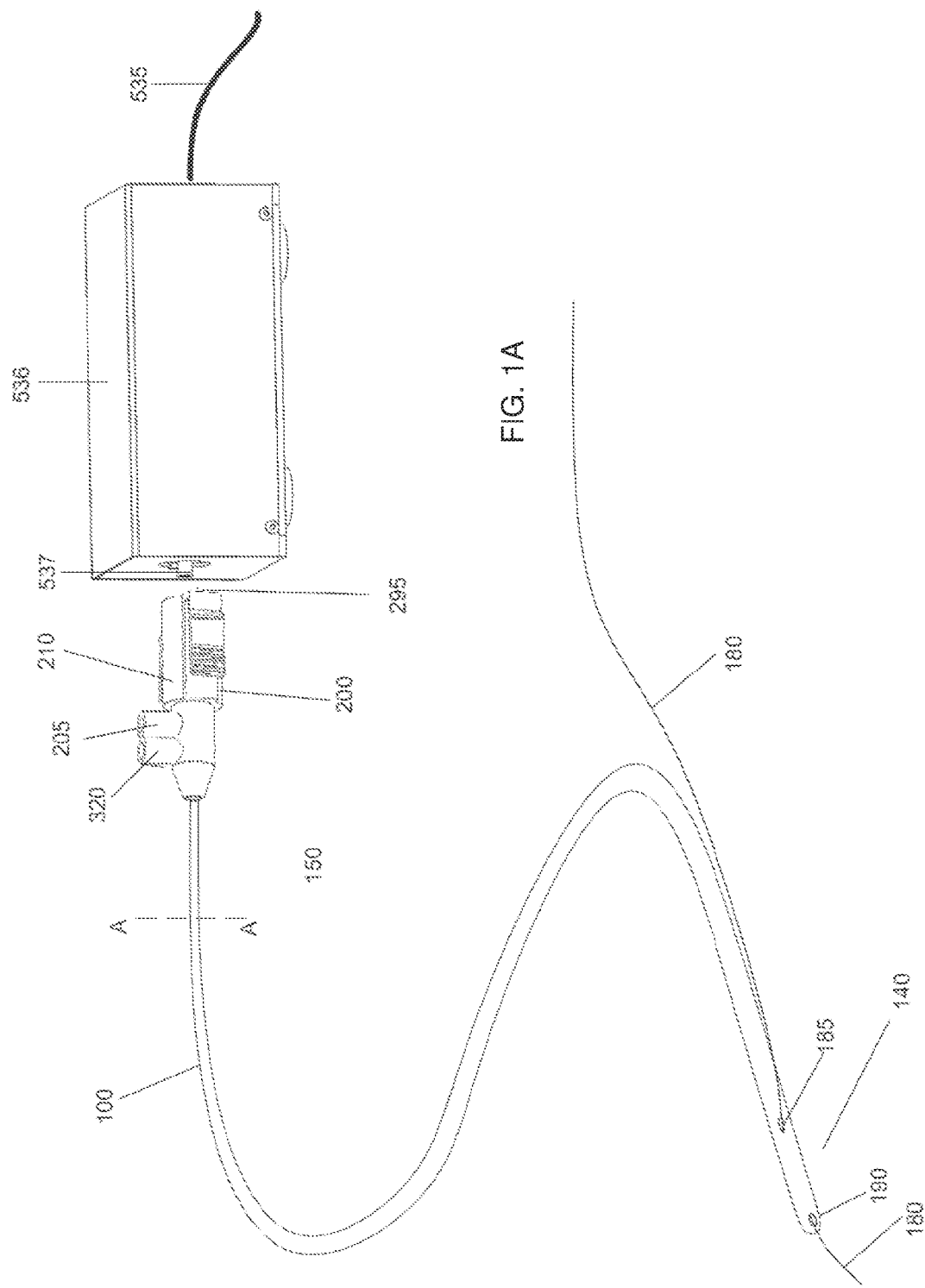

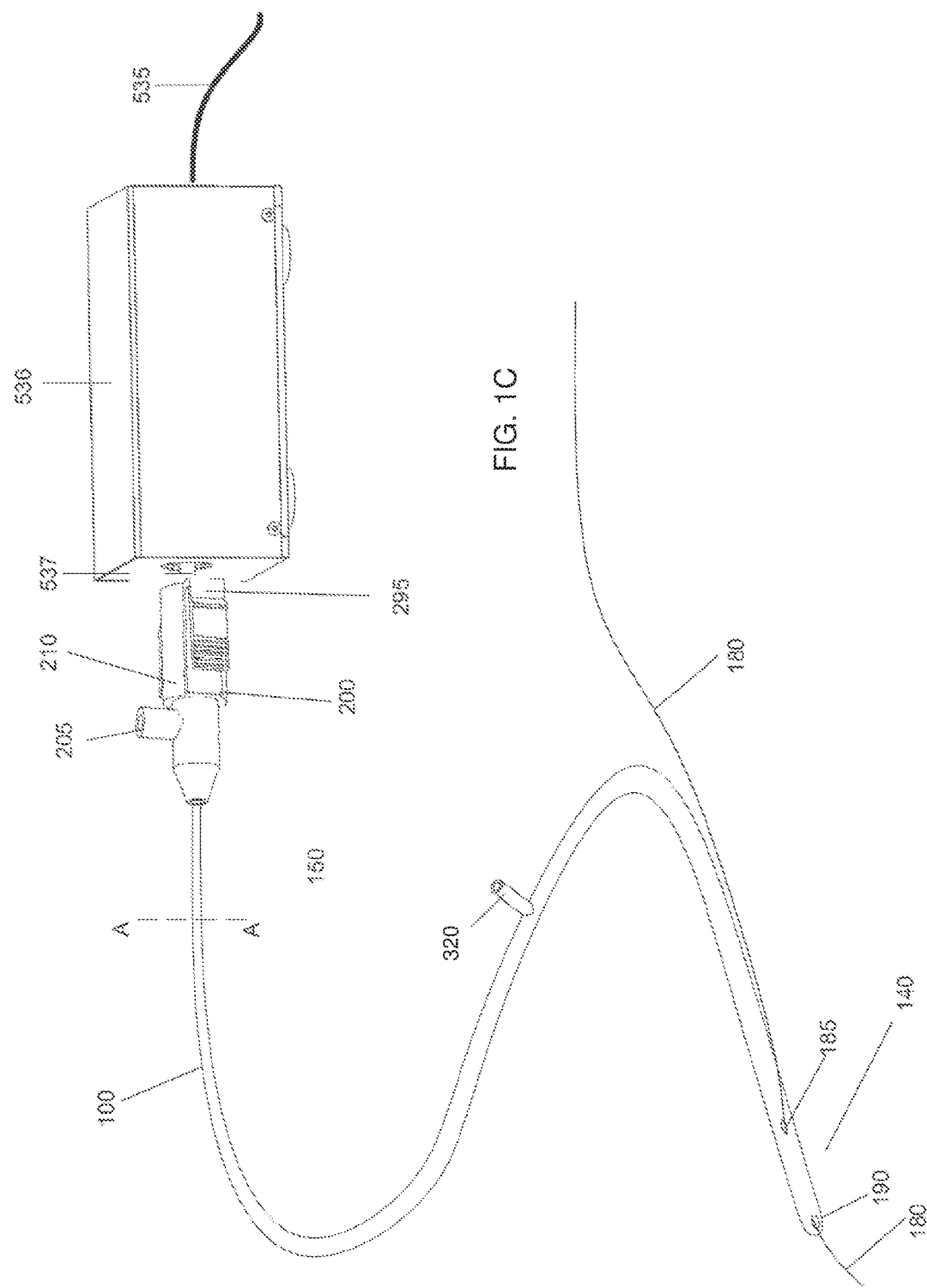

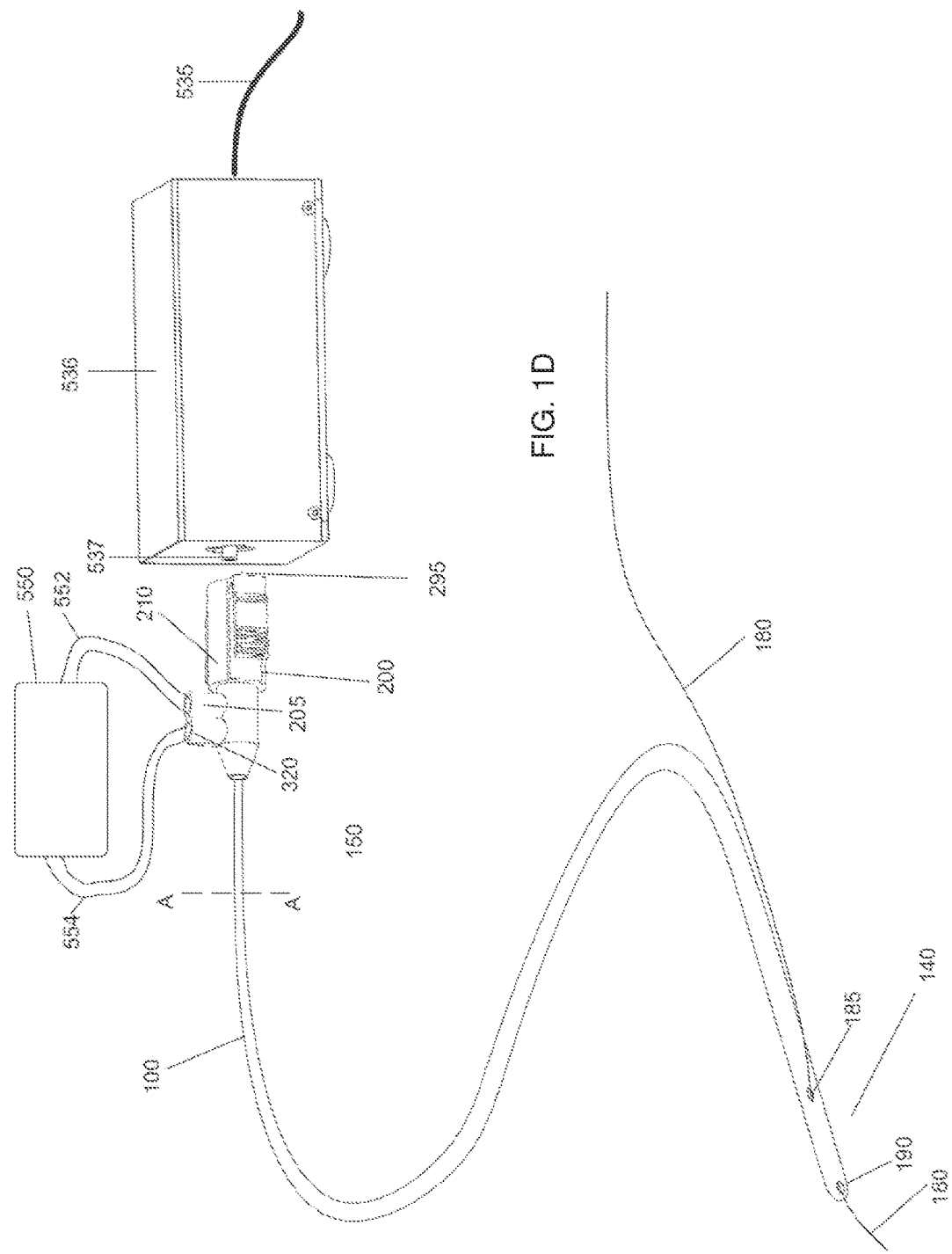

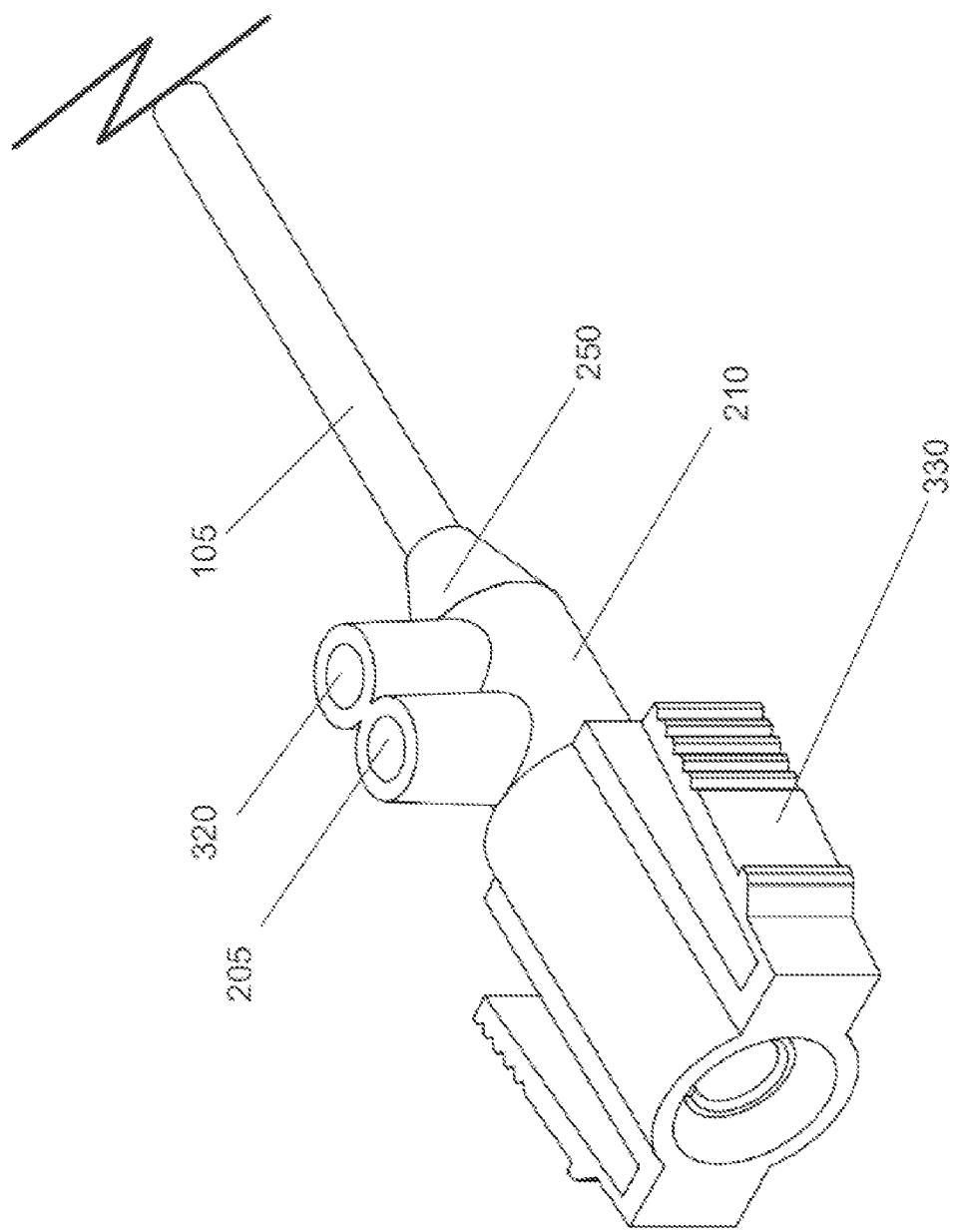

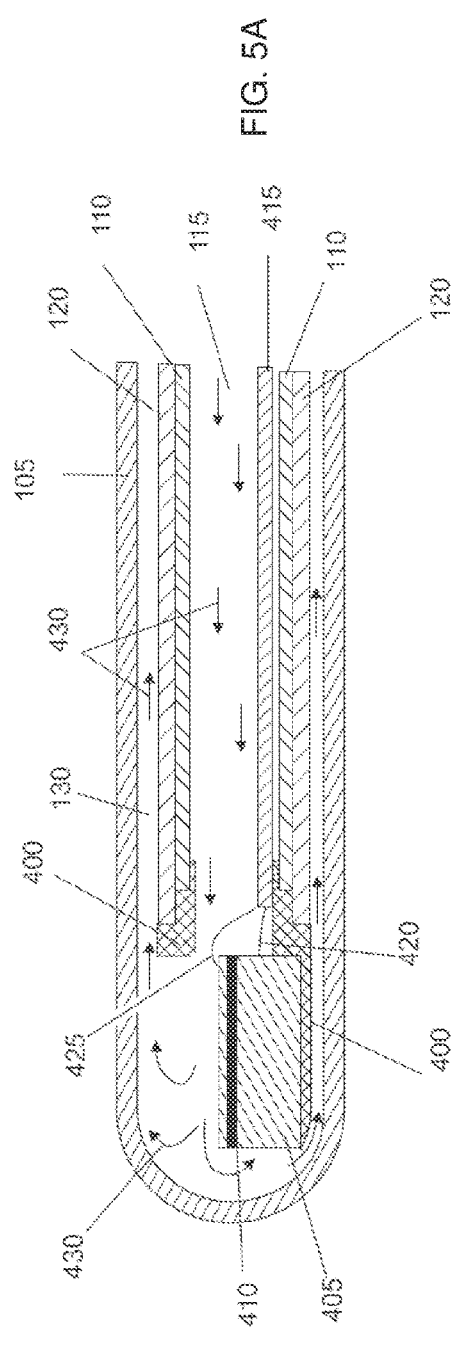
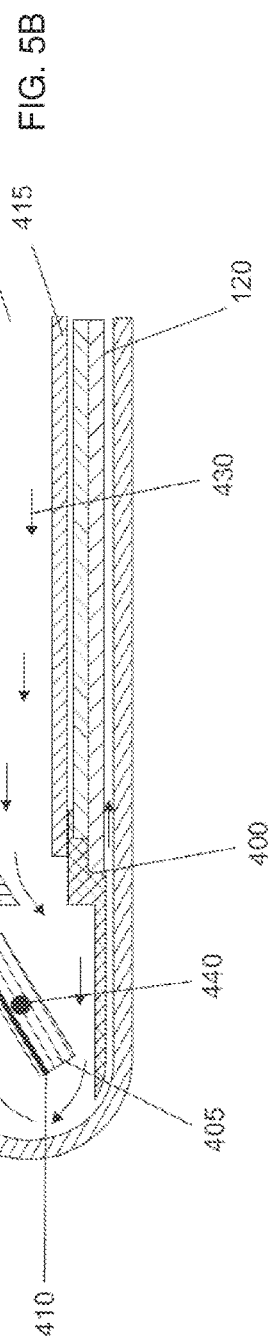
FIG. 5A
FIG. 5B

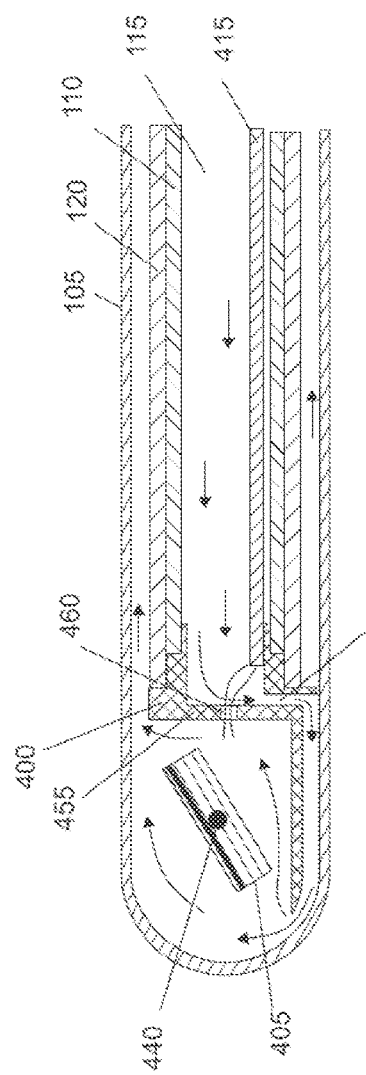
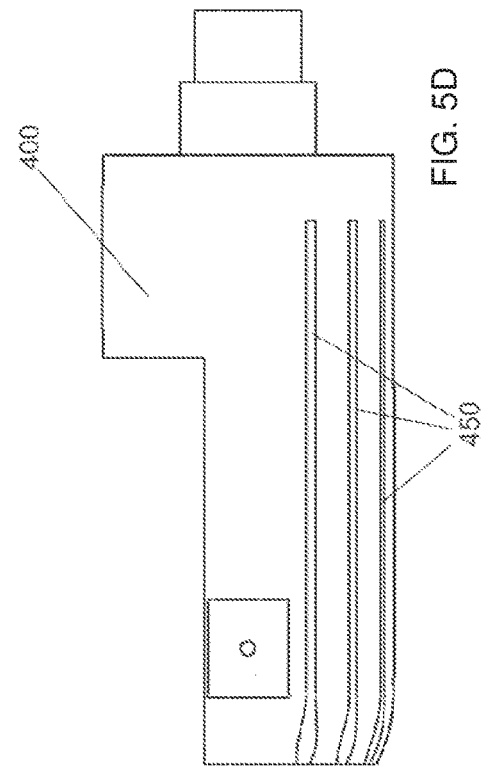
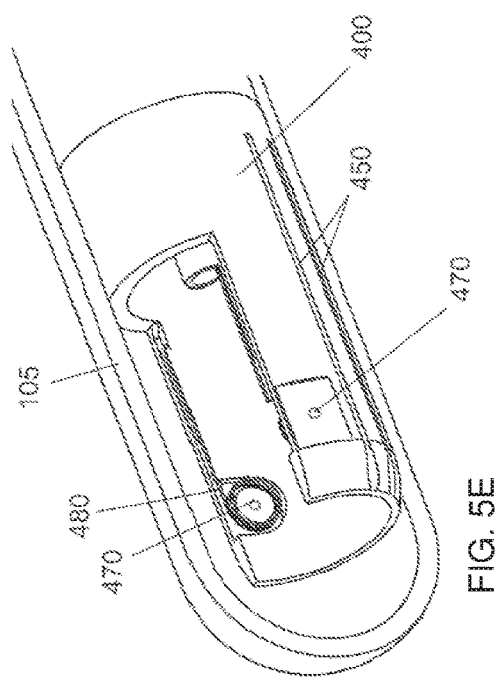
FIG. 5C
FIG. 5D
FIG. 5E

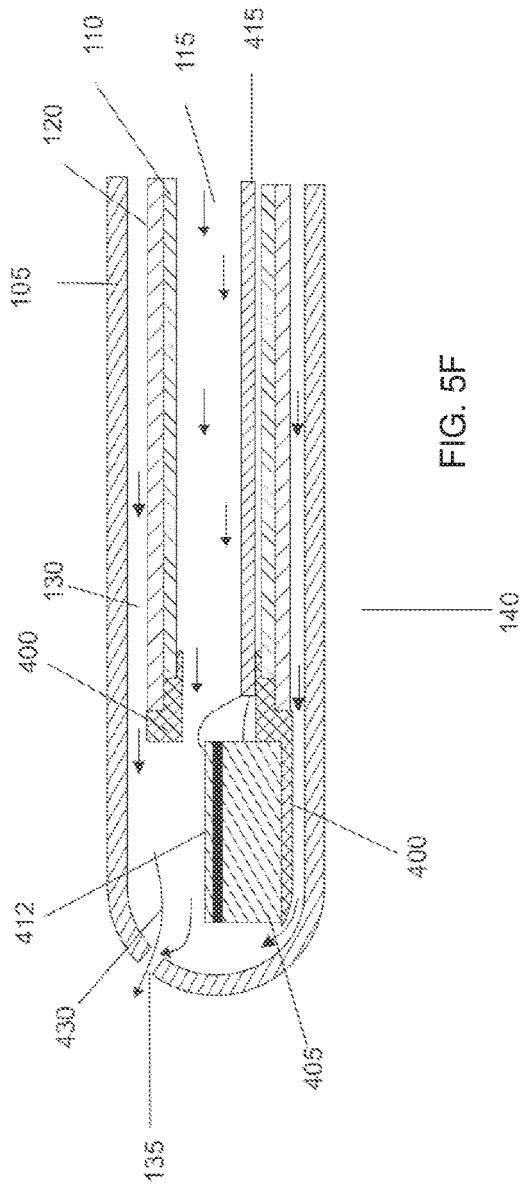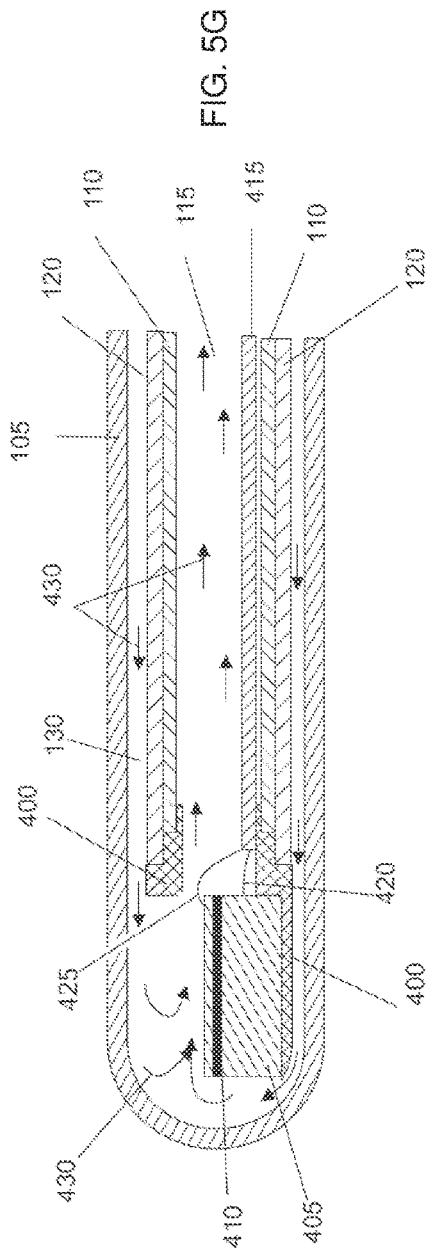

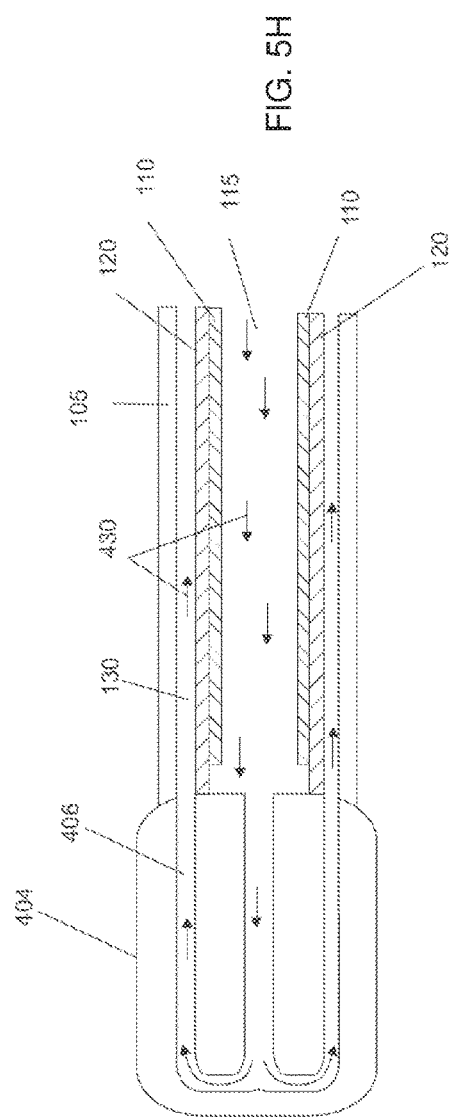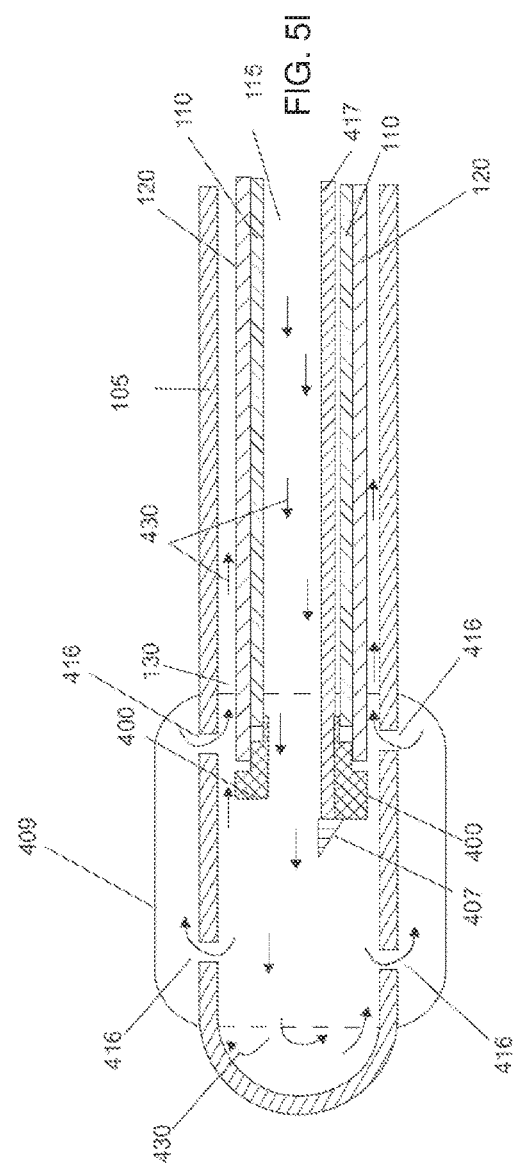

MEDICAL PROBE WITH FLUID ROTARY JOINT

CROSS-REFERENCE TO RELATED APPLICATION

This application is a continuation of U.S. application Ser. No. 13/482,896, titled "MEDICAL PROBE WITH FLUID ROTARY JOINT" and filed on May 29, 2012, which claims priority to U.S. Provisional Application No. 61/490,930, titled "CATHETER WITH FLUID ROTARY JOINT" and filed on May 27, 2011, the entire contents of which are incorporated herein by reference.

BACKGROUND

The present disclosure relates to medical probes, and more particularly, the present disclosure relates to medical probes, such as catheters, in which a fluid is transported within a portion of the probe.

Medical probes, such as catheters, are commonly used in minimally invasive procedures for the diagnosis and treatment of medical conditions. Such procedures may involve the use of intraluminal, intracavity, intravascular, and intracardiac catheters and related systems. When performing such procedures, imaging and treatment catheters are often inserted percutaneously into the body and into an accessible vessel of the vascular system at a site remote from the vessel or organ to be diagnosed and/or treated. The catheter is then advanced through the vessels of the vascular system to the region of the body to be treated.

The catheter may be equipped with an imaging device employing an imaging modality such as optical imaging, optical spectroscopy, fluorescence, infrared cardiac endoscopy, acoustic imaging, photo-acoustic imaging, thermography, and magnetic resonance imaging. For example, an ultrasound or optical imaging device may be employed to locate and diagnose a diseased portion of the body, such as, a stenosed region of an artery. The catheter may also be provided with a therapeutic device, such as those used for performing interventional techniques including balloon angioplasty, laser ablation, rotational atherectomy, directional atherectomy and the like.

Imaging catheters, such as intravascular and intracardiac ultrasound catheters, typically require the catheter body to be purged of air during operation. The purging is performed to support the efficient propagation, within the catheter body, of imaging energy generated or detected by one or more internal transducers. For example, an ultrasound transducer housed within an intravascular ultrasound catheter is typically immersed in a liquid during operation to support the efficient coupling of acoustic waves from the transducer to the external medium to be imaged.

The fluid is commonly introduced into the catheter by a procedure referred to as "flushing" the catheter, where fluid is injected into the catheter via a port at the proximal end. This fluid, which is typically a liquid such as saline or sterile water, travels along the length of the inner main lumen of the catheter and purges air out of a port near the distal tip of the catheter. Other catheters do not support flushing of the catheter through ports available outside the body. Such catheters typically require manual injection of a fluid coupling medium to the distal tip of the catheter via a needle attached to a syringe. It is desirable to making flushing a safe, simple, quick and effective procedure. In many applications, it is also desirable to fluidly isolate inner portions of catheters from the anatomic environment into which they are used. Generally, the catheter is flushed with liquid prior to insertion of the catheter into the vasculature if the physician wishes to minimize the probability of introducing air bubbles into the bloodstream.

Many intravascular imaging catheters are designed such that, during use, blood can enter the catheter via the distal flushing port. This blood can interfere with the mechanical or imaging performance of the catheter. For example, if the blood were to form a thrombus within the imaging catheter, it could damage delicate components within the catheter and/or be expelled during a subsequent flushing procedure, potentially leading to embolic complications. Furthermore, the use of a distal flushing port that potentially releases particles or soluble materials from inside the catheter into the vasculature reduces design flexibility with respect to the selection of materials used within the catheter. It also requires that the fluid used for flushing be physiologically compatible, such as saline.

In some cases, a catheter may be inadequately flushed, and the resulting imaging quality can be significantly degraded. For example, air bubbles on ultrasound transducers or optical components substantially reduce image quality if they lie within regions in which acoustic waves or optical energy travel.

As an alternative to flushing via a proximal port and allowing fluid to exit via a distal port, some catheters have been designed with a separate lumen as part of the imaging catheter to deliver fluid to the distal end of the catheter, allowing the fluid to "backfill" the main lumen of the catheter. Alternatively, the separate lumen can used as a venting lumen, where the fluid is introduced via the main lumen, and the separate lumen allows air to escape.

The separate flushing lumen takes up space and is often made as small as possible to avoid an excessive increase in the diameter of the catheter. This can unfortunately be a significant limitation in the case of intravascular catheters, which typically require a compact configuration in order to enable delivery into the vasculature. For example, catheters currently employed for intravascular ultrasound and intracardiac echocardiography are approximately 0.8 to 4 mm in diameter, where the smaller sizes of probes can be delivered more distally within the vascular tree of the coronary anatomy as the vessel caliber tapers down or as diseased vessels are stenosed. Furthermore, such probes may be advanced across the atrial septum from the right atrium into the left atrium of the heart via either a pre-existing communication, such as a patent foramen ovale, or via a communication created during a procedure, such as a trans-septal puncture. Smaller sizes generally allow for interrogation of a larger portion of the coronary or cardiac anatomy or may allow for the creation of smaller holes through which to access the desired anatomic regions. It is therefore desirable for a probe and its components to be contained within a minimal outer diameter or minimal cross-sectional area to enable imaging.

SUMMARY

Embodiments herein provide a catheter including an external sheath, a rotatable conduit housed within the external sheath, and a fluid rotary joint having a rotatable insert that places an inner lumen of the rotatable conduit in fluid communication with an external port under rotation of the rotatable conduit. The rotatable insert is rotatably supported within an outer housing and may include a channel structure including an external annular channel. The rotatable conduit is received within a longitudinal portion of the channel structure such that the inner lumen is in fluid communication with the external port through the annular channel under rotation of the rotatable conduit. The external sheath may define an outer lumen that may be in fluid communication with the inner lumen at a location remote from a proximal portion of the catheter, and the outer lumen may be in fluid communication with a secondary port. The rotatable conduit may be housed within a torque cable that is connected to the rotatable insert.

Accordingly, in a first aspect, there is provided a medical probe comprising: an external sheath; a rotatable fluid conduit housed within the external sheath, the rotatable fluid conduit including an inner lumen; and a fluid rotary joint comprising: an outer housing including an external port, wherein the external sheath is connected to the outer housing; a rotatable insert having an inner channel, wherein the rotatable insert is rotatable within the outer housing, and wherein a proximal portion of the rotatable fluid conduit is received within the inner channel of the rotatable insert, such that the inner channel is in fluid communication with the inner lumen; wherein the inner channel is in fluid communication with the external port under rotation of the rotatable fluid conduit; and wherein the rotatable insert is connectable to an external rotational drive mechanism.

In another embodiment, there is provided a fluid rotary joint for use with a medical probe, the medical probe including an external sheath housing a rotatable fluid conduit, the rotatable fluid conduit having an inner lumen, the fluid rotary joint comprising: an outer housing including an external port, wherein the outer housing is connectable to the external sheath of the medical probe; a rotatable insert including an inner channel, wherein the rotatable insert is rotatable within the outer housing, and wherein the inner channel of the rotatable insert is configured to receive a proximal portion of the rotatable fluid conduit, such that the inner channel is in fluid communication with the inner lumen; wherein the inner channel is in fluid communication with the external port under rotation of the rotatable fluid conduit; and wherein the rotatable insert is connectable to an external rotational drive mechanism.

A further understanding of the functional and advantageous aspects of the disclosure can be realized by reference to the following detailed description and drawings.

BRIEF DESCRIPTION OF THE DRAWINGS

Embodiments of the disclosure will now be described, by way of example only, with reference to the drawings, in which:

FIG. 1A shows a catheter system employing a fluid rotary joint to provide a working fluid to an inner lumen of the catheter.

FIG. 1C shows an alternate embodiment of a fluid rotary joint where the secondary port is positioned in a location other than on the proximal connector.

FIG. 1D shows a fluid rotary joint that is controlled by an external pump.

FIG. 4A shows a perspective view of the outer housing of the fluid rotary joint and FIG. 4B shows an exploded longitudinal cross-sectional view.

FIGS. 5A-5I provide cross-sectional views of various embodiments of a distal end of a catheter comprising an inner fluid lumen, where FIG. 5A shows fluid flowing over an ultrasonic transducer, FIG. 5B shows an embodiment in which the working fluid flows around an ultrasonic transducer, FIGS. 5C, 5D, and 5E show views of an embodiment in which the working fluid is deflected prior to encountering an ultrasonic transducer, FIG. 5F shows the fluid exiting via a distal exit port, FIG. 5G shows an alternative direction of fluid transport as compared to that shown in FIG. 5A, FIG. 5H shows the use of a fluid rotary joint in a thermal application where fluid enters a network of channels distributed around a mechanical tool for cooling or heating the tool and FIG. 5I shows the use of a balloon catheter employing the fluid rotary joint.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

Embodiments disclosed below provide a catheter with a rotatable fluid conduit having an inner lumen that is in fluid communication at its proximal end with a fluid rotary joint. Embodiments described below enable transport of a working fluid through the rotatable inner lumen, thus providing advantages and benefits related to system size, performance, compatibility and flexibility.

Figure 1B:
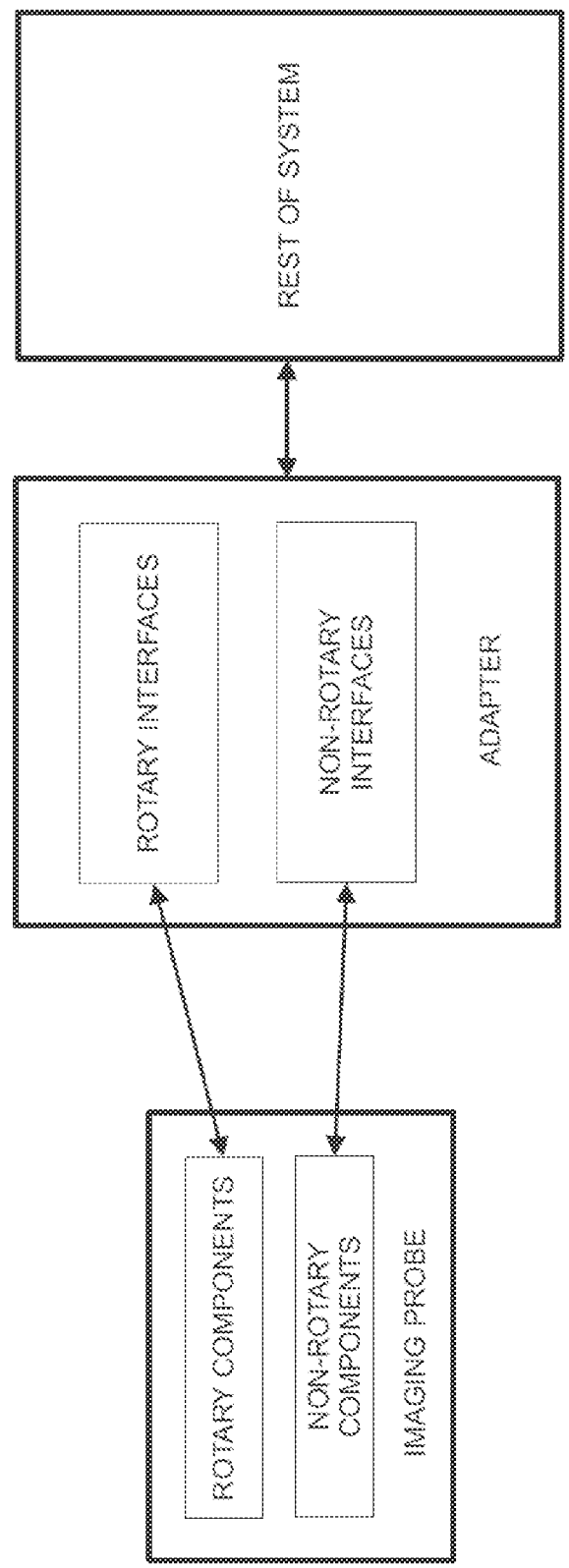
FIG. 1B illustrates the interfacing of the rotary and non-rotary components of the system.
Figure 2A:
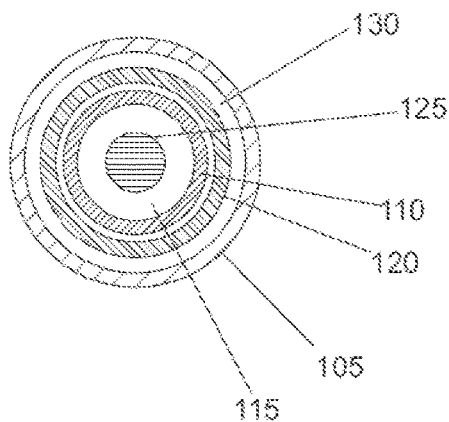
FIG. 2A shows a cross sectional view across section A-A in FIG. 1A showing a coaxial embodiment.

Referring to FIGS. 1 and 2(a), catheter 100 is shown having an external sheath 105. External sheath 105 is a hollow, elongate shaft made of physiologically compatible material and having a diameter suitable to permit insertion of the hollow elongate shaft into bodily lumens and cavities. External sheath 105 may be flexible, or may be rigid for applications where a rigid imaging probe may be desired, such as for some bronchoscopic, laryngoscopic or otoscopic applications.

Catheter 100 includes proximal connector 200 at its proximal end. Proximal connector 200 comprises a fluid rotary joint including outer housing 210 and a rotatable insert 215 (shown in FIG. 3a and FIG. 3b). Proximal connector 200 is also connectable to a patient interface module 536, which couples other external rotatable and non-rotatable components to rotating and non-rotating components of catheter 100. Patient interface module 536 may have one or more cables 535 that receive power and enable communication with a console, such as an image processing and display system. Although the fluid rotary joint is shown the present example implementations as being provided at a proximal end of catheter 100, it is to be understood that any component along the length of the rotating components of catheter system 560 may contain the fluid rotary joint.

For clarity, "rotatable" or "rotating" components refer to components that rotate with a rotatable shaft. An example of a rotatable component is a torque cable (described and shown below), at least a portion of which lies within an external sheath of catheter 100 and is able to rotate independent of the external sheath. "Non-rotating" components refer to components that do not rotate with the rotatable shaft, but may nonetheless be rotated, such as under manual manipulation of the catheter's outer housing or external sheath.

FIG. 2(a) shows a cross-section as indicated at section A-A in FIG. 1a. Torque cable 120 is disposed within external sheath 105 for rotating a fluid conduit 110 and may contain one or more optical and/or electrical channels housed within active conduit 125. Such torque cables are typically formed from strands of wires arranged in various manners (for example, as taught by Crowley et al. in U.S. Pat. No. 4,951,677, titled "Acoustic Imaging Catheter and the Like"), but can also include tubing, such as hypotubing made of stainless steel or nitinol. Torque cables can also be substituted with rotatable conduits formed from materials such as polymeric tubing, such as those made of polyimide or PEEK. Torque cables can also be made with different configurations along their length, such as a hypotube construction along a proximal extent and strands of braided or coiled wires along a distal extent.

In some embodiments, the outer catheter diameter is in the range of approximately 0.8 to 4 mm. Also, in some embodiments, the length of the catheter portion is approximately 5 to 150 cm in length. Although such sizes are typical sizes for imaging catheters, it is to be understood that other sizes may be suitable for other applications involving medical probes.

Fluid conduit 110 houses inner lumen 115 and may, in some embodiments, be made from liquid impermeable materials such as, but not limited to, PEEK, nylon, polyimide, PEBAX, PTFE, stainless steel, and nitinol. Fluid conduit 110 may be impermeable to liquids along all or most of its longitudinal extent. Fluid conduit 110 and torque cable 120 are rotatable and rotate in unison under the application of an external torque to torque cable 120, as further described below. If present, one or more active conduits 125 within torque cable 120 would also rotate in unison with torque cable 120.

A diagnostic or therapeutic assembly, such as an imaging assembly comprising an imaging transducer, or a treatment device such as a laser ablation emitter, may be connected to active conduit 125, at a location remote from the proximal end of catheter 100, for the transmission of power, imaging energy, and/or received signals. At least a portion of the diagnostic or therapeutic assembly rotates in unison with torque cable 120. In the case where active conduit 125 contains one or more electrical channels, active conduit 125 may be electrically insulated from working fluid contained within catheter 100.

Catheter 100 further includes non-rotating outer lumen 130, which may be in fluid communication with inner lumen 115 at a location remote from a proximal end of fluid conduit 110. In some embodiments, outer lumen 130 is fluidly isolated from its surrounding environment within the vasculature. Optionally, as shown in FIG. 5f, outer lumen 130 may exit catheter 100 at one or more locations, for example, at distal flush port 135 at a distal portion 140 of catheter sheath 105.

Referring again to FIG. 1a, at proximal end 150, catheter 100 is received by proximal connector 200. The fluid rotary joint, which is housed within proximal connector 200, provides fluid communication of inner lumen 115 with non-rotating fluid port 205 during rotation of torque cable 120 and fluid conduit 110. For example purposes, the fluid rotary joint and fluid port 205 are illustrated as incorporated into proximal connector 200.

Figure 6:
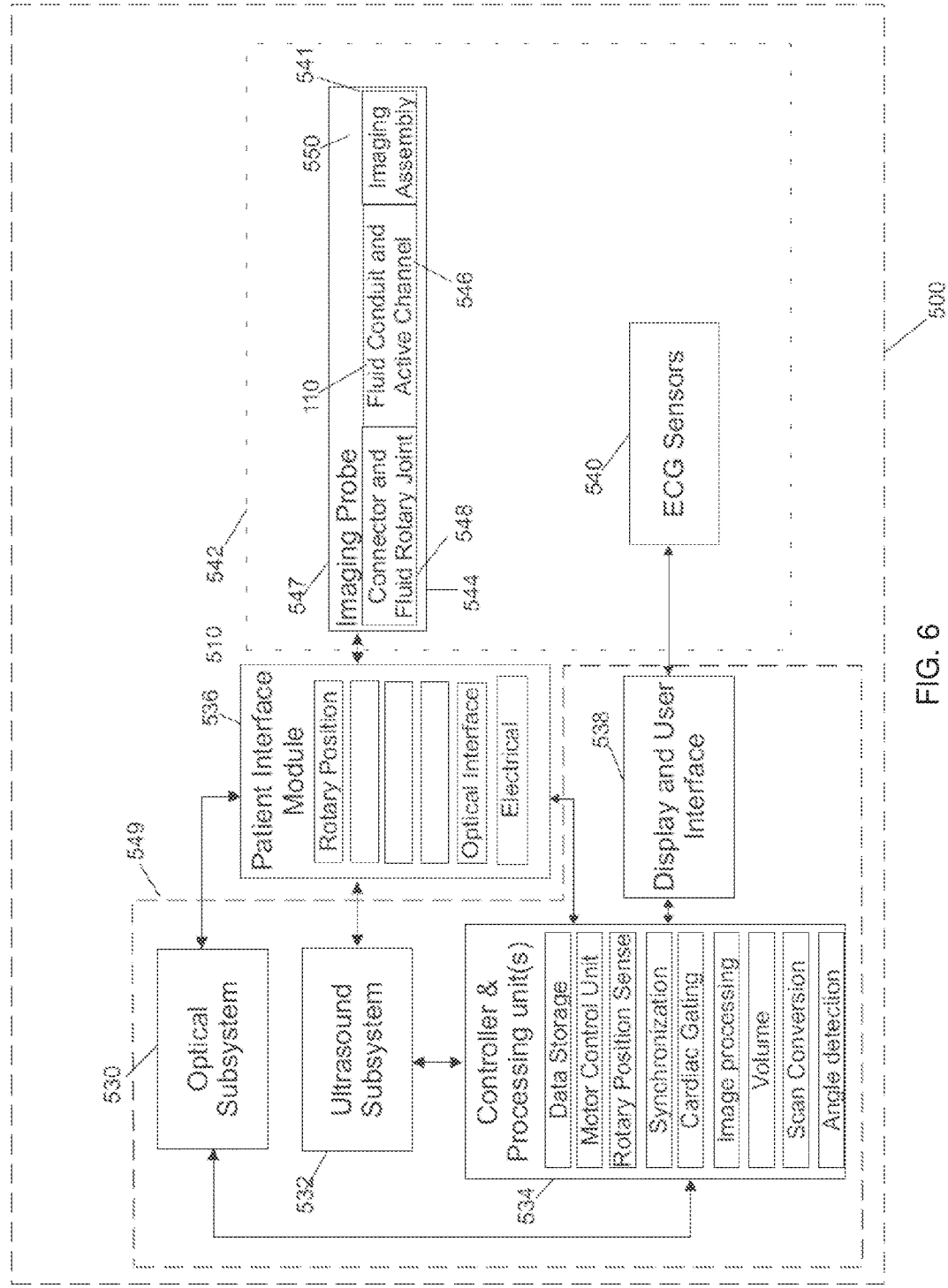
FIG. 6 shows a system level diagram illustrating various components of the catheter system.

As shown in FIG. 1(b), patient interface module 536 performs, in part, as a rotational adapter that mechanically supports non-rotating components, rotationally drives rotatable components, and couples other rotating components of the system to signal processing subsystems and other subsystems (such as those shown in FIG. 6). Patient interface module 536 may also include a rotational drive mechanism, whereby a controllable motor is mechanically coupled to a rotatable portion 537 (shown in FIG. 1) of patient interface module 536. Such mechanical coupling between rotatable portion 537 of patient interface module 536 and controllable motor (not shown) may be provided by belts, pulleys, gears and other coupling mechanisms known to those skilled in the art. Alternatively, rotatable portion 537 may be directly coupled to a hollow bore shaft of a controllable motor. Furthermore, as shown in FIG. 1a and FIG. 4a (described further below), outer housing may include a latching mechanism 330 for securing the fluid rotary joint to a patient interface module, as described below.

Electrical and/or optical channels within active conduit 125 (such as a coaxial electrical cable or optical fiber) are directly or indirectly fed through the fluid rotary joint and are coupled, through patient interface module 536, to back-end subsystems. Accordingly, patient interface module 536 facilitates transmission of signals within any fibers and/or wires to the appropriate subsystems.

Referring to FIG. 1(b), the adapter can include slip rings, optical rotary joints and other such implements for electrically or optically coupling a rotary component to a non-rotary component in the rest of the system and to enable communication of necessary electrical and optical signals with the rest of the system. A conductor mounted onto a rotating component in catheter 100 can be coupled to non-rotating conducting elements via metallic slip rings and springs, metallic slip rings and brushes or other commonly known methods of forming conductive contact between a stationary conductor and a rotary conductor.

In some embodiments, active channel 125 may additionally or alternatively include a fiber optic that is in optical communication with one or more optical components provided in an imaging assembly, where the imaging assembly may be connected to torque cable 120. Examples of suitable optical components include a lens, a light-deflecting element, and an optical spacer. As shown in FIG. 1(a), the catheter optionally includes guidewire 180, shown in a "rapid exchange" configuration, where guidewire 180 enters catheter external sheath 105 at first guidewire port 185, and exits catheter 100 at second guidewire port 190. It is to be understood that guidewire may alternatively be employed in an "over the wire" configuration.

FIG. 1(a) also illustrates an example embodiment in which proximal connector 200 also includes a non-rotating secondary fluid port 320. As further described below, secondary port 320 may be in fluid communication with an outer, non-rotating lumen of catheter 100, where the outer lumen is in fluid communication with the inner lumen at a location within catheter 100 that is remote from proximal end of catheter 100, thereby forming a closed internal fluid path connecting port 205 with secondary port 320.

FIGS. 1(c) and 1(d) illustrate two alternative embodiments of the catheter system. In FIG. 1(c), an example embodiment is shown in which secondary port 320 is located along the external sheath, at a location that is remote from the proximal end of catheter 100.

FIG. 1(d) illustrates an embodiment in which a pump mechanism 550 is shown for circulating a fluid between port 205 and secondary port 320 with flow channels 552 and 554. Pump mechanism may be any suitable type of pump, such as, for example, peristaltic, centrifugal or diaphragm pumps. Alternatively, a non-recirculating pump may be used, and channel 554 may be directed to a waste container.

Figure 2B:
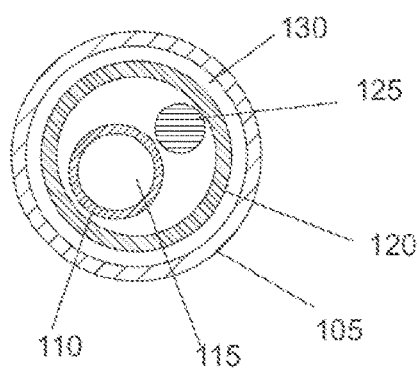
FIG. 2B shows an off-axis embodiment of FIG. 1A and and FIG. 2C shows a coaxial embodiment of FIG. 1A with the flushing conduit integrated closely with a torque cable.

FIG. 2(b) illustrates another embodiment of the catheter cross section (section A-A) in which fluid conduit 110 and active conduit 125 are separately housed within torque cable 120, where fluid conduit 110 functions as a dedicated flow channel that does not house active conduit 125.

Although outer lumen 130 is shown in FIGS. 2(a) and (b) to lie between torque cable 120 and external sheath 105, it is to be understood that outer lumen 130 may also be in fluid communication with the region between torque cable 120 and fluid conduit 110. For example, torque cables are often highly permeable to fluids, enabling the flow of working fluid through the wall of torque cable 120.

Figure 2C:
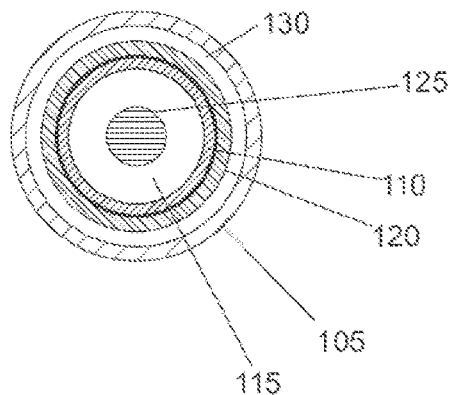

Alternatively, torque cable 120 may be made less permeable or impermeable to the working fluid, for example by either by coating or otherwise integrating a liquid impermeable material such as a polymer with the wall of the torque cable. Such an embodiment is illustrated in FIG. 2(c), where torque cable 120 is directly lined with fluid conduit 110 as a lining on the inner surface of the torque cable. Alternatively, the lining can be on the outside of the torque cable, embedded within the torque cable or a combination thereof.

Although many of the embodiments disclosed herein include a torque cable for providing rotary motion to an assembly or device remote from a proximal end of catheter 100, it is to be understood that any suitable shaft, tube or rotary conduit may be included. In some embodiments, the rotary conduit providing rotary motion to the remote assembly or device, and the inner conduit may be one in the same. For example, in some implementations, torque cable 120 may be impermeable, or may be substituted with an impenetrable rotatable conduit (such as a hypotube component), whereby the torque cable or rotary conduit may also act as fluid conduit 110.

Catheter 100 may include features (such as an external sheath comprising two or more telescoping segments) that allow rotating components, such as torque cable 120 and fluid conduit 110, to translate longitudinally in unison within external sheath 105. This translational capability is commonly referred to as "pullback" capability. In such an embodiment comprising telescoping segments of the external sheath, the telescoping segments may have a tight seal between each other, such as by being constructing with tight tolerances between the two parts or by inclusion of one or more o-rings, viscous fluids or similar sealing components.

Figure 3A:
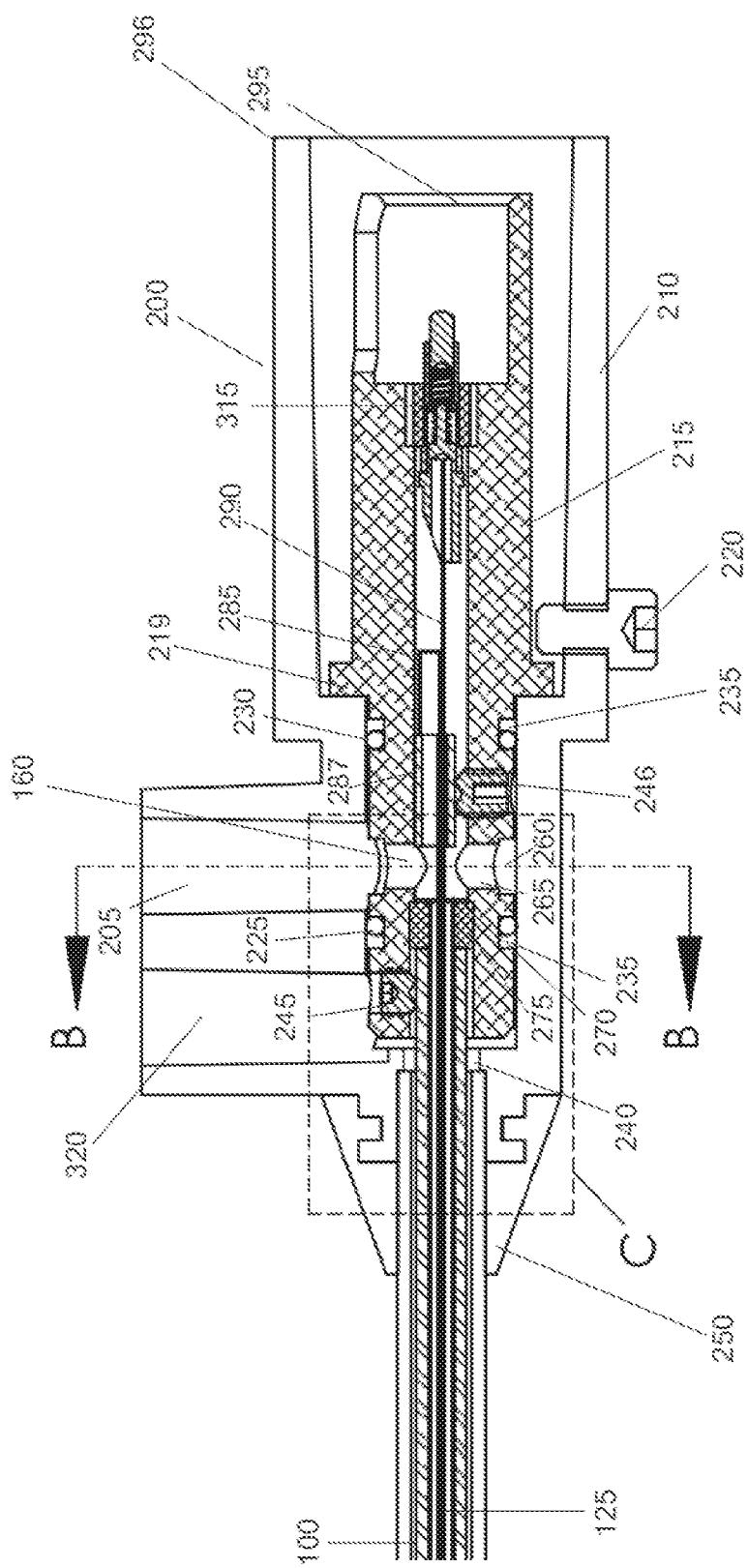
FIG. 3A provides a cross-sectional view through a fluid rotary joint, showing the outer housing and rotatable insert.
Figure 3B:
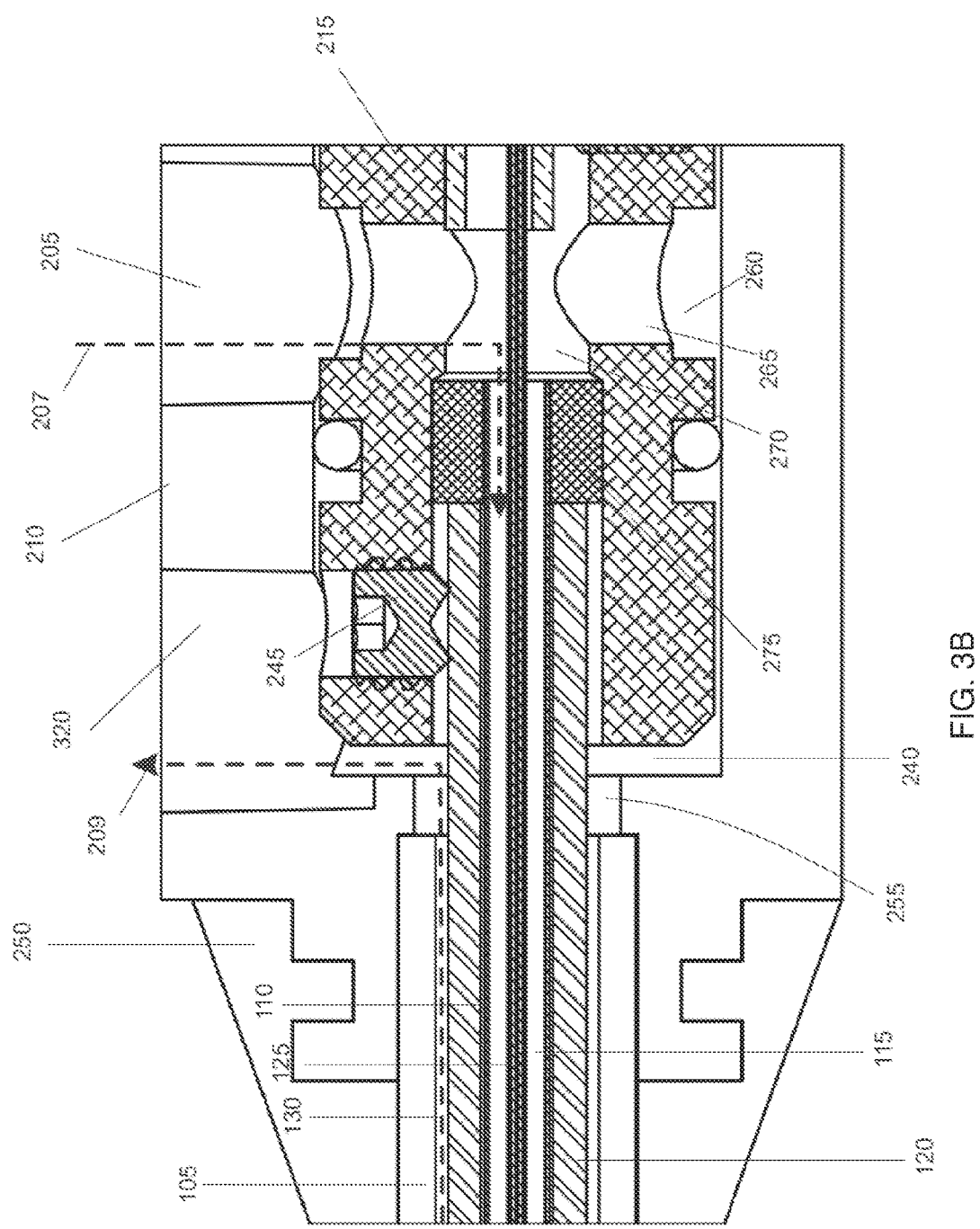
FIG. 3B shows a close-up view of region C in FIG. 3A.

FIGS. 3(a) and 3(b) illustrate an embodiment of fluid rotary joint 160 that is configured for transporting working fluid through non-rotating primary port 205 and into rotatable inner lumen 115 of catheter 100, as shown by flow path 207 in FIG. 3(b). Fluid rotary joint 160 includes non-rotating outer housing 210 (also shown in FIG. 4(a)) and rotatable insert 215 that rotates within housing 210. As shown in FIG. 3(b), which provides a detailed view of the region marked "C" in FIG. 3(a), a proximal portion of rotatable conduit 110 is received within rotatable insert 215 such that inner lumen 115 is in fluid communication with primary port 205 under rotation of rotatable conduit 110.

As shown in FIGS. 3(a)-(d), primary port 205, annular flow channel 260, lateral flow channel 265 and longitudinal flow channel 270, which form chambers of fluid rotary joint 160, are in fluid communication with inner lumen 115 of fluid conduit 110. A fluid seal between the radially outermost extent of rotatable insert 215 and the inner surface of outer housing 210 is provided by distal seal 225 and proximal seal 230 (such as o-rings) that are housed within seal appropriately sized recesses within rotatable insert 215. Distal seal 225 and distal seal insert 275 (described in further detail below) prevent fluid within the chambers of fluid rotary joint 160 from being in direct fluid communication with outer lumen 130 of catheter 100, with the exception of the fluid path provided by inner lumen 115 at a distal portion of catheter 100.

The rotatable insert 215 may, in some embodiments, have a size ranging from approximately 3 to 10 mm in outer diameter and 20 to 50 mm in length.

Figures 3C, 3D:
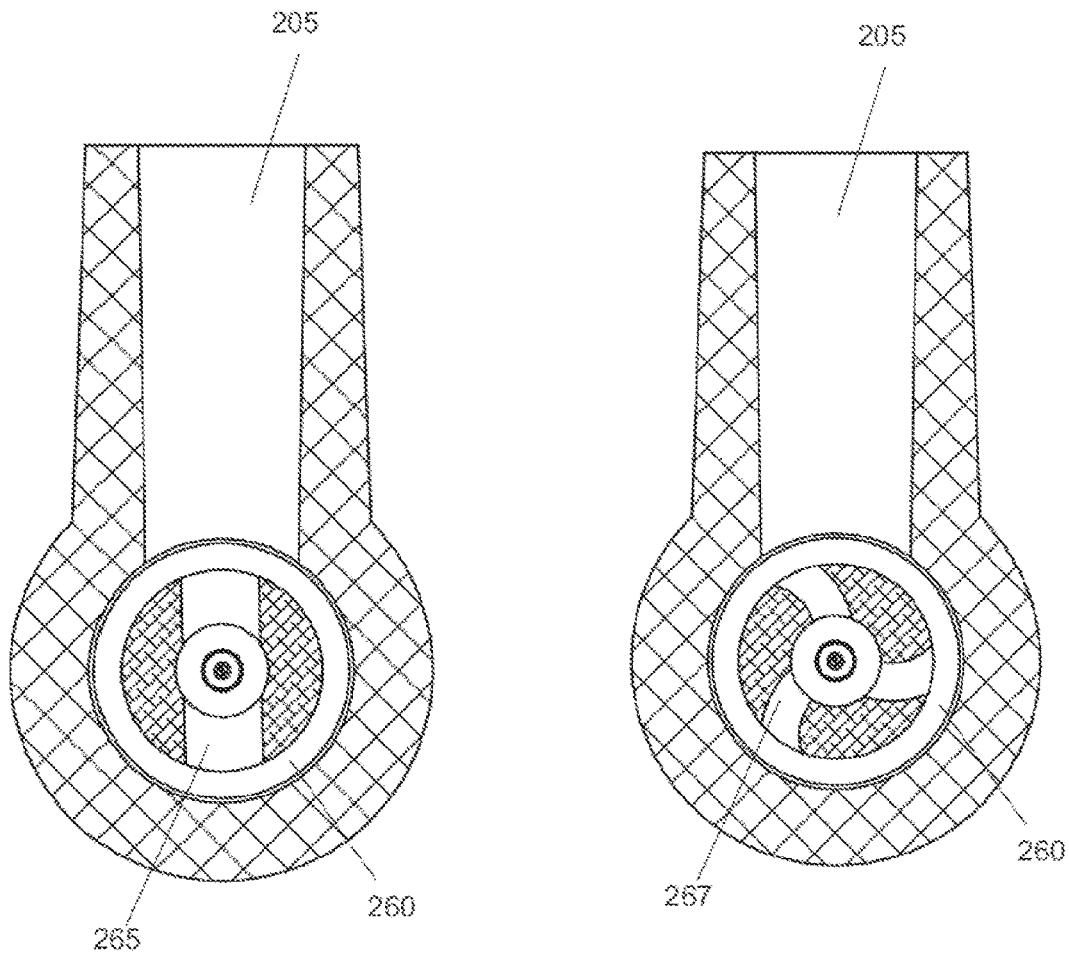
FIG. 3C shows a cross-section through line B-B in FIG. 3A, showing an example configuration of the lateral and annular channels.
FIG. 3D shows an alternative cross-section through line B-B in FIG. 3A using non-radial lateral channels.

FIGS. 3(c)-3(d) illustrate various example embodiments of the cross-sectional configuration of the fluid rotary joint along line B-B of FIG. 3(a). While two lateral flow channels are shown in FIG. 3a, any number of radial flow channels between longitudinal flow channel 270 and annular flow channel 260 may be included. When two or more radial flow channels are implemented, they may be uniformly distributed around the circumference of annular flow channel to minimize vibrations. Furthermore, while FIG. 3(c) illustrates an embodiment in which lateral flow channels 265 are radial flow channels, it is to be understood that the lateral flow channels need not be radial in shape, and can be provided with a non-radial geometry, for example, as illustrated by channels 267 in FIG. 3(d).

Figure 3F:
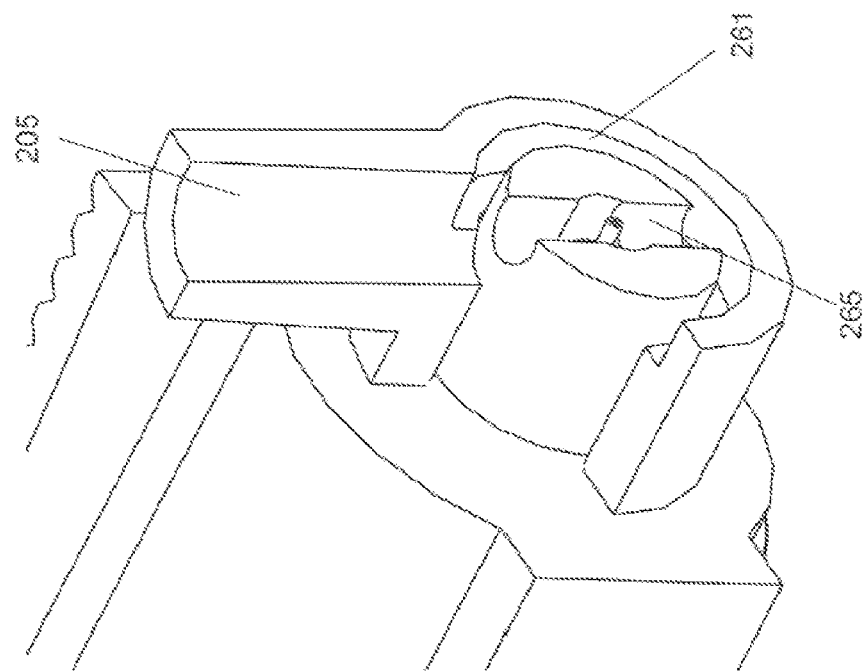
FIG. 3F illustrates a cutaway view of an alternative embodiment in which the annular channel is formed within the outer housing.
Figure 3E:
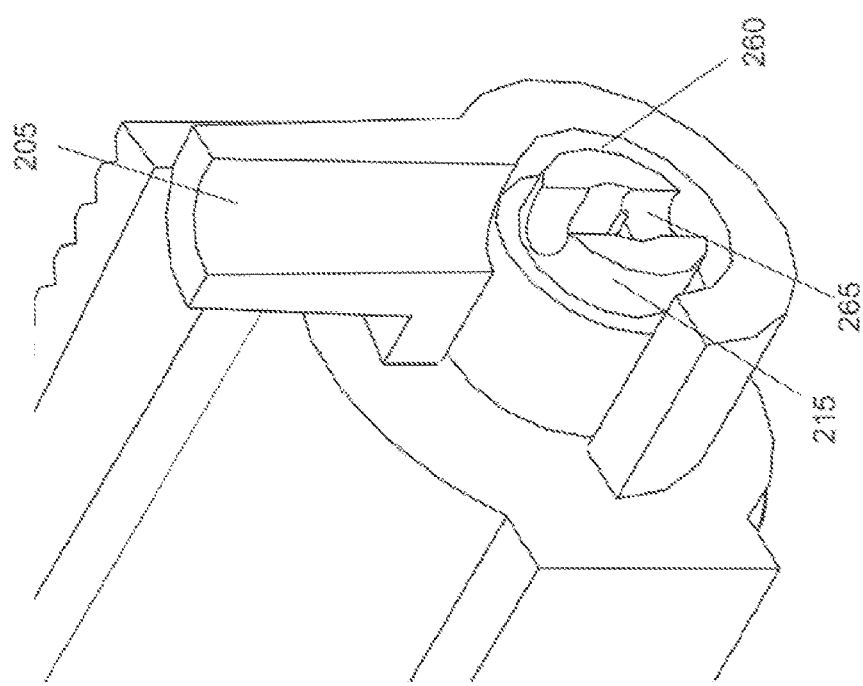
FIG. 3E shows a cutaway view of the embodiment of FIGS. 3A-C where the annular channel is formed within the rotary insert

FIGS. 3(e) and 3(f) show cut-away views illustrating optional configurations of the annular channel. In FIG. 3(e), annular channel 260 is shown as being formed within rotatable insert 215. An alternative embodiment is shown in FIG. 3(f), where annular channel 261 is shown as being formed within outer housing 210. In other embodiments, the annular channel may be formed in both rotatable insert 215 and in outer housing 210.

In one embodiment, rotatable insert 215 is rotationally supported by rotatable shaft 537 of patient interface module (or of a suitable rotational drive mechanism). Rotatable insert 215 may be longitudinally retained within outer housing 210 by retaining screw 220, which may abut against collar 219 and prevent rotatable insert 215 from translating in a longitudinal direction. Rotatable insert 215 may alternatively or additionally be rotatably supported by a bearing (such as, for example, a Teflon™ bearing). This bearing may exist in the proximal connector 200 or an interfacing component.

As further described below, distal seal 225 may be a partial seal, so that fluid within chambers of fluid rotary joint 160 is in fluid communication with both inner lumen 115 and outer lumen 130 of catheter 100, but whereby the distal seal 225 increases the resistance to flow between the chambers of fluid rotary joint 160 and outer lumen 130 of the catheter. Such a distal seal with a partial seal may be desirable for embodiments similar to that shown in FIG. 5f. Proximal seal 230 contributes to preventing fluid from leaking from fluid-filled chambers of the catheter 100 and proximal connector 200 out of the proximal extent 296 of proximal connector 200.

The inclusion of distal seal 225 increases (e.g. doubles) the running friction, because there are two seals instead of only the one proximal seal 230. This increase in friction can cause an undesirable heat generation, leading to temperatures that may be potentially unsafe to the user or destructive to other components. Three factors for decreasing the running friction are: rotational speed, seal diameter, and seal compression. The rotational speed may be determined by the medical probe functionality, and may be reduced in some applications in order to generate less heat while still providing a suitable rotation rate. The diameters of proximal seal 230 and distal seal 225, however, can be kept small to reduce heat generation and be designed with minimal precompression force. To minimize temperature rise, the fluid rotary joint can be adapted to dissipate the generated heat to the ambient air quickly. For example, the walls of outer housing 210 can be kept thin, and, if possible, be made of a thermally conductive material, such as aluminum. It may be beneficial to include external features on the outer housing for dissipating internally generated heat. These features may include heat sinking fins and other known heat sinking structures.

As shown in FIGS. 3(a) and 3(b), secondary port 320 may be attached to, or formed within, a non-rotating component, such as non-rotating outer housing 210 of proximal connector 200, thereby forming a closed internal fluid path to and from a distal region of catheter 100. Secondary port 320 may optionally be a Luer connector of opposite gender to that of primary port 205. Alternatively, optional distal flush port 135, shown in FIG. 5f, may act as a substitute for secondary port 320. As described further in FIGS. 5(a)-(i), working fluid flowing within inner lumen 115 may be brought into fluid communication with outer lumen 130 in a region of catheter 100 that is remote to the proximal end of catheter 100.

As further illustrated in FIGS. 3(a) and 3(b), rotatable insert 215 may be connected to a proximal end of torque cable 120 by a fastener or clamping mechanism, such as set screw 245. Accordingly, the rotation of rotatable insert 215 is coupled to torque cable 120, which in turn rotates the rotating components of catheter 100 housed within external sheath 105.

As described above, rotatable insert 215 is further connectable at its proximal end 295 to a rotatable drive assembly for imparting and controlling rotation to the rotating components of catheter 100 housed within or connected to torque cable 120. The rotatable drive assembly may be provided within patient interface module 536, as noted above.

With further reference to FIGS. 3(a) and 3(b), working fluid transported through primary port 205 in outer housing 210 is in fluid communication with annular flow channel 260 provided in rotatable inset 215, which itself is in fluid communication with radial flow channel 265 that connects annular channel 260 to longitudinal flow channel 270. Working fluid in longitudinal channel 270 is in fluid communication with inner lumen 115.

As shown in FIG. 3(b), fluid conduit 110 may extend through or otherwise couple with an inner bore in distal seal insert 275 such that the inner surface of fluid conduit 110 and inner bore of distal seal insert 275 form a substantially leakproof channel between inner lumen 115 and longitudinal flow channel 270. Distal seal insert 275 is shown as being secured into place via a friction fit (e.g. press-fit) to create a seal. Distal seal insert 275 may be replaced by a functionally similar feature directly integrated into rotatable insert 215. Alternatively, distal seal insert 275 may include an outer annular channel (not shown) for housing a sealing material, such as an o-ring, glue, caulking or other suitable sealing material.

In an alternative example implementation, distal seal insert 275 can be omitted, such as when the torque cable 120 is impermeable to fluid flow and acts as both a torque cable 120 and fluid conduit 110.

FIGS. 3(a) and 3(b) illustrate the case where a central conductor 290 is connected through ground tube 287 to the central conductor of connector 315 (for example, an SMB connector). An outer conductor 285 may be connected to ground tube 287, and connected to ground through the body of rotatable insert 215 (for example, by using set screw 246 to press against conductor 285). Alternatively, if rotatable insert 215 is not electrically conductive, conductors 285 and 290 can be electrically connected to electrical connector 315 via other suitable conductors or conductive means, such as soldering, use of conductive epoxy, laser welding, and crimping.

Figure 3G:
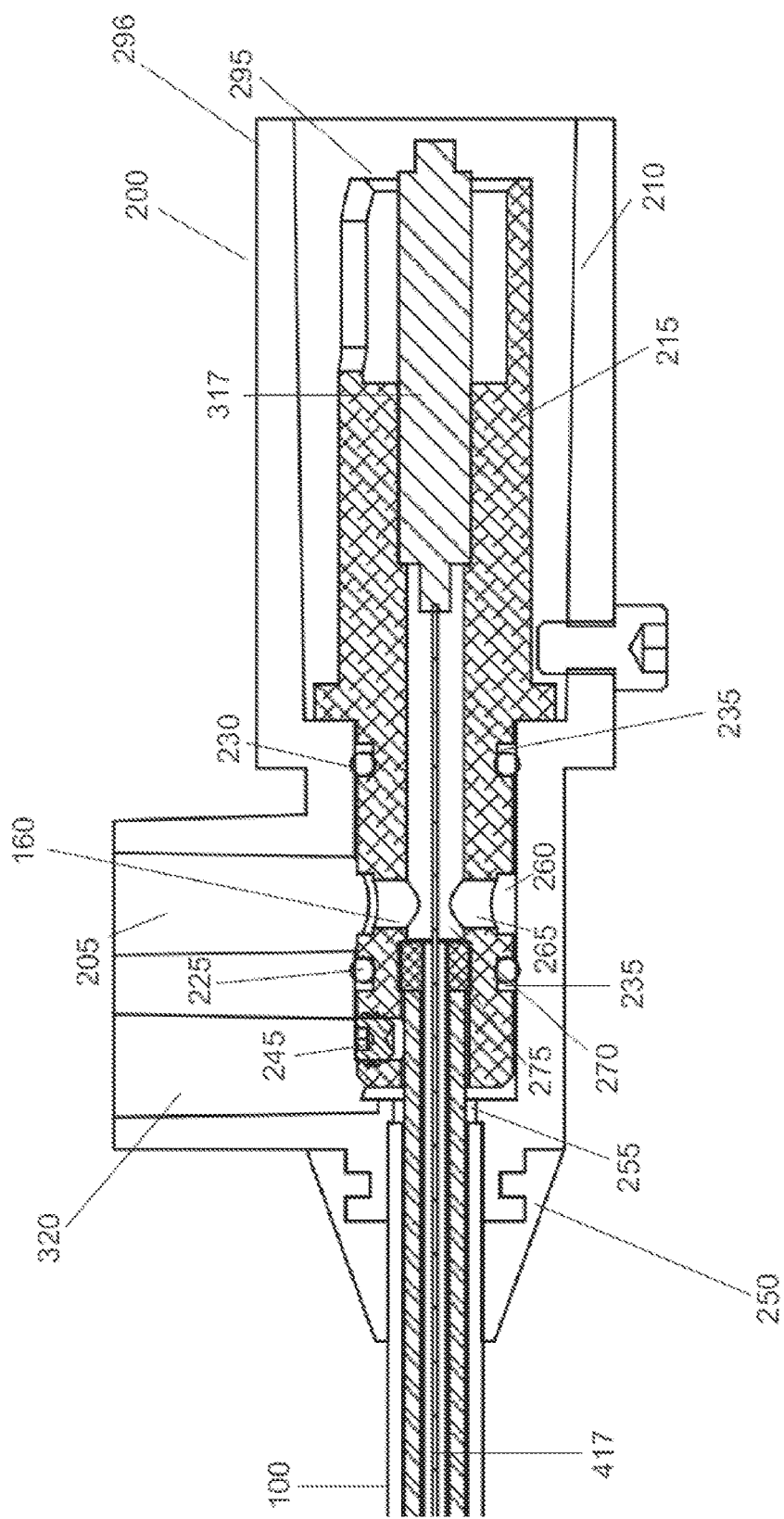
FIG. 3G provides a cross-sectional view through another embodiment of a fluid rotary joint where the active conduit contains an optical channel.
Figure 3H:
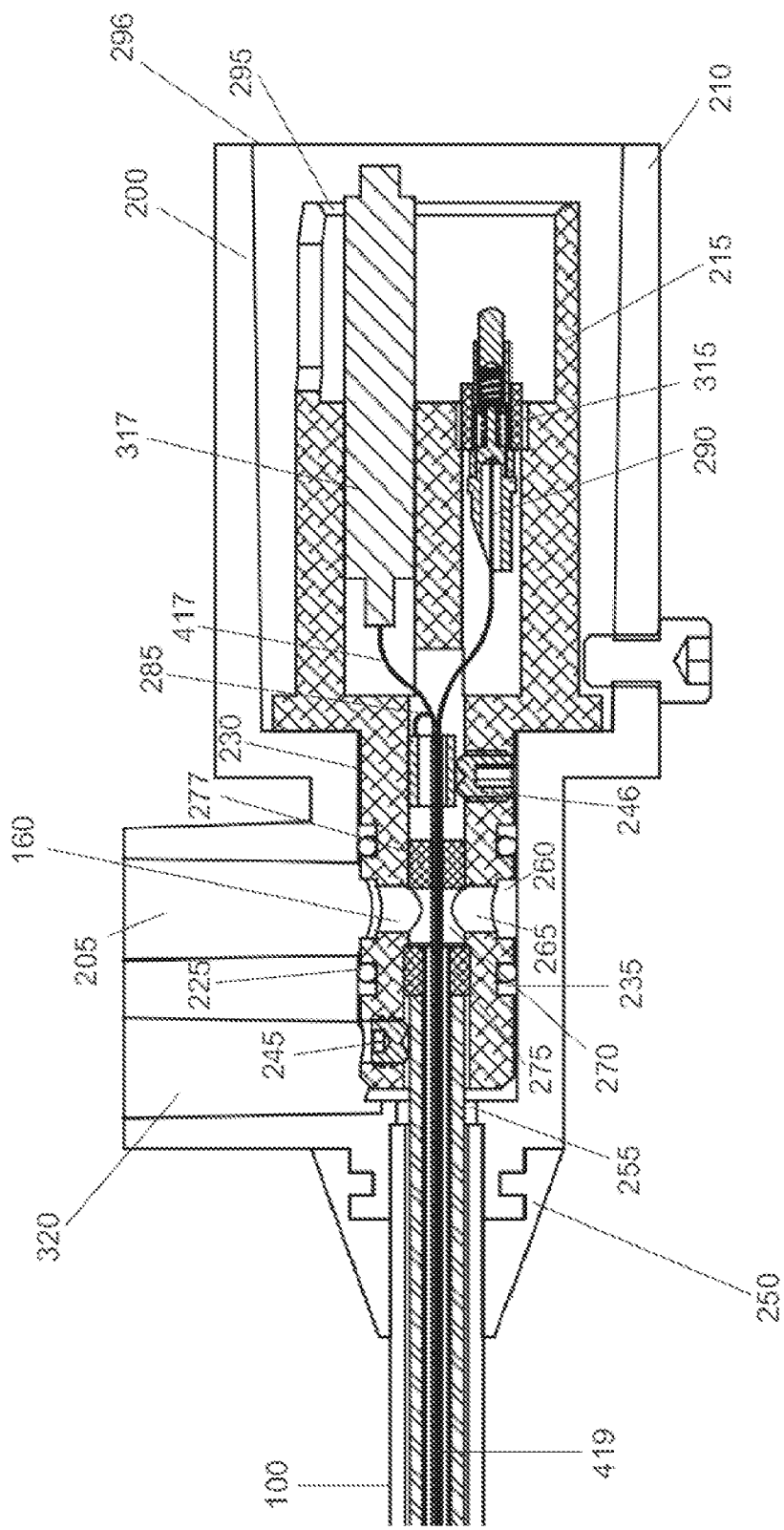
FIG. 3H provides a cross-sectional view through an embodiment of a fluid rotary joint in which the active conduit includes both optical and electrical channels.

In an alternative embodiment, in which it is important for the electrical conductors to not be in electrical communication through the working fluid, a proximal seal insert 277 shown in FIG. 3h may be provided in order ensure that working fluid does not enter the region in which the conductors are separated and electrically routed. Such a proximal seal insert may include outer an annular channel for housing a sealing material, such as an o-ring, glue, caulking or other suitable sealing material. Alternatively, a proximal seal insert may be press-fit into place to create a seal, or the proximal seal insert may be replaced by a functionally similar feature directly integrated into rotatable insert 215. The bore of the proximal insert may be sealed with a sealing material or via tight tolerances between the bore and the active conduit, such that fluid in longitudinal chamber 270 would not leak beyond proximal insert within rotatable insert 115. As shown in the Figures, the active conduit may house a pair of electrical channels, such as a twisted pair or coaxial cable.

As noted above, annular channel 260 maintains fluid communication between primary port 260 and radial channel 265 during rotation of rotatable insert 215. In another embodiment, annular channel 260 may not be present, such that radial channel 265 extends to an outer surface of rotatable insert 215 and forms an aperture at a given angular position. Such an embodiment enables fluid communication between primary port 260 and radial channel 265 when radial channel 265 is aligned with primary port 260. This alignment may be achieved during an initial flushing operation in which catheter 100 is pre-flushed prior to a procedure. Alternatively, the annular channel may be incorporated into outer housing 210 rather than rotatable insert 215.

FIG. 3(b) further illustrates how working fluid within outer lumen 130 is brought into fluid communication with chamber 240 in outer housing 210 and secondary port 320 through flow path 209. An outer surface of external sheath 105 is secured to an inner surface of outer housing 210, which may be at a distal portion of outer housing 210. For example, as shown in the Figure, outer housing 210 may include, at its distal end, a strain relief boot 250 to which external sheath 105 is secured (for example, using an epoxy, UV glue, cyanoacrylate or other leak-tight adhesive). Strain relief boot 250 may include one or more deformable materials such as rubber, silicone, polyurethane, other polymers or other suitable materials.

A portion of external sheath 105 is shown extending into outer housing 210 such that outer lumen 130 is maintained and placed in fluid communication with chamber 240 through gap 255. Chamber 240 is shown as a small longitudinal section within outer housing, overlapping only a small portion of secondary port 320. In other embodiments, chamber 240 may extend over a larger longitudinal section, such that chamber 240 overlaps with a larger portion. Gap 255 is maintained by coaxially securing external sheath 105 and torque cable 120 to outer housing 210 and rotatable insert 215, respectively. As described above, torque cable 120 may be permeable to flow, thus enhancing fluid communication between outer lumen 130 and chamber 240.

FIG. 3(g) illustrates an embodiment in which active conduit 125 includes optical fiber 417, which is routed through the central bore of distal seal insert 275 in a manner similar to that described above. Optical fiber is connected to optical connector 317, which may be a standard optical connector such as an angle polished connector. As noted above, an optical rotary joint may be provided within patient interface module 536 for coupling light from a rotating optical fiber to a non-rotating optical fiber or optical element.

It is to be understood that the embodiments disclosed above are not limited to a single active channel, and that two or more different active channels may be housed within torque cable 120. In other embodiments, more than one electrical or optical active channel may be provided. In one embodiment, one or more active channels may facilitate signal delivery relating to imaging modalities, such as optical or acoustic imaging modalities. In other embodiments, one or more active channels may provide power or actuating signals to other non-imaging active elements located at a distal portion of catheter 100. Examples of non-imaging active elements include therapeutic treatment elements such high intensity focused ultrasound transducers, laser ablation emitters, cryo-ablation and others.

FIG. 3(h) illustrates an embodiment in which active conduit 125 includes both an optical channel and an electrical channel in active channel 419. Both optical fiber 417 and electrical conductors 285, 290 may be routed through the central bore of distal seal insert 275, and can be further routed through to connect to their respective connectors as described for the single active channel embodiments.

In another embodiment, the secondary port may be located at a different longitudinal position than shown in FIGS. 1a, 3, 4 and 6. For example, secondary port 320 may be provided in a separate assembly that is located remote from proximal connector 200, as shown in FIG. 1c. In yet another embodiment, secondary port may be replaced by an opening in external sheath 105, where the opening is positioned at a longitudinal location that is intended to lie within a subject, which may be employed for flushing a cavity or lumen.

FIG. 4(a) shows a perspective view of proximal connector 200 that contains primary port 205 and secondary port 320. The proximal end of external sheath 105 of catheter 100 is shown extending from the distal end of proximal connector 200.

Figure 4B:
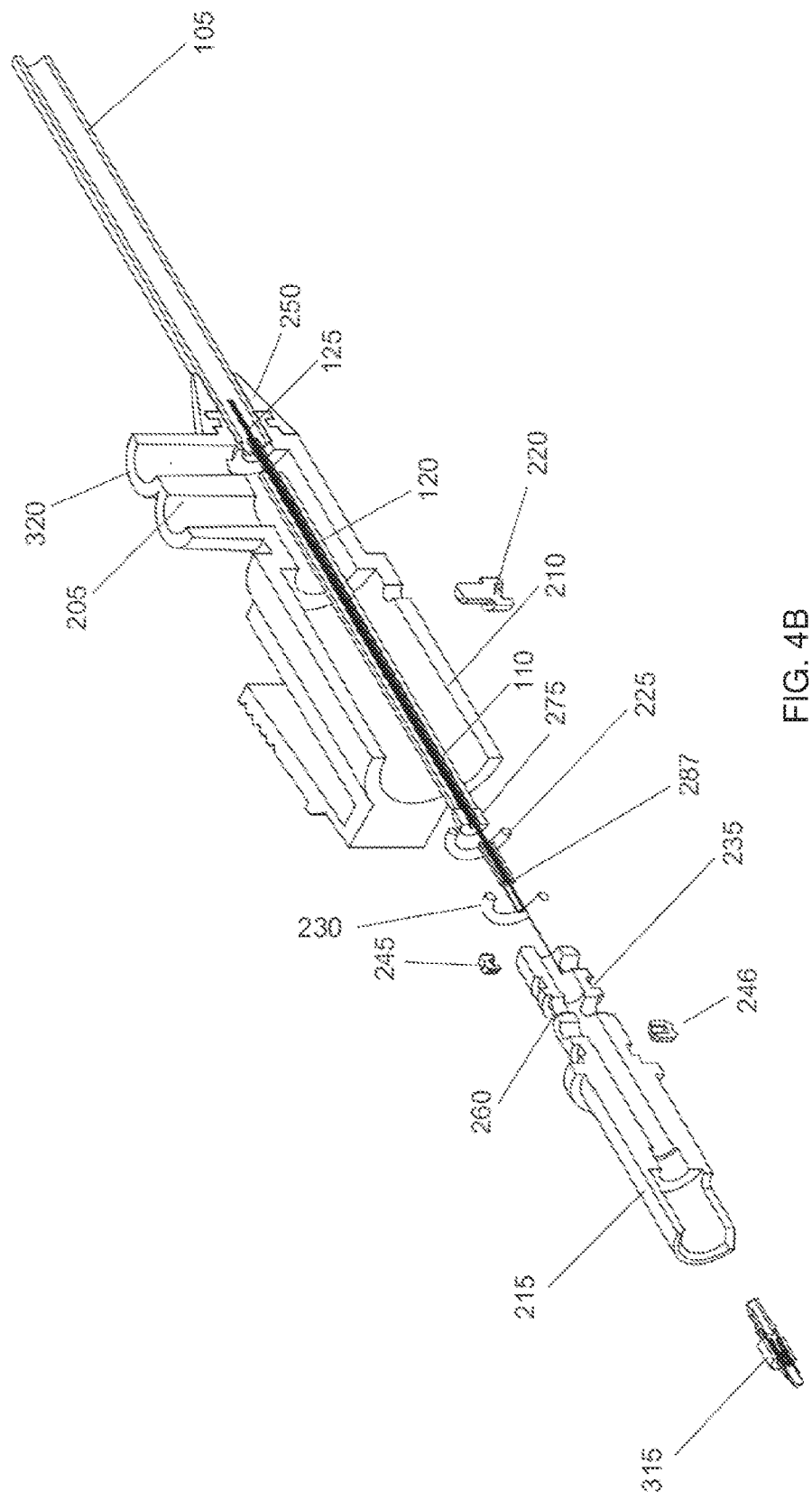

FIG. 4(b) shows an exploded longitudinal cross-sectional view of proximal connector 200. Abbreviated lengths of active conduit 125, fluid conduit 110, torque cable 120 and external sheath 105 are shown to simplify the illustration of the construction of fluid rotary joint within proximal connector 200.

FIGS. 5(a)-(e) illustrate various embodiments whereby inner lumen 115 is brought into fluid communication with outer lumen 130 at a distal end 140 of catheter 100. Optional remote housing 400, which is mechanically coupled to torque cable 120 and fluid conduit 110, may support a remote assembly, such as ultrasonic transducer 405 having active portion 410, shown as an example assembly in the Figures. Ultrasonic transducer 405 is electrically contacted with signal 425 and ground 420 lines, which are connected to coaxial cable 415 that is housed within torque cable 120 and externally connected or connectable to a signal acquisition system.

In the embodiment shown in FIG. 5(a), working fluid is delivered to distal end 140 of catheter through inner lumen 115, and passes over ultrasonic transducer 405 before being returned to the proximal end of catheter 100 within outer lumen 130. Arrows 430 illustrate an example direction of flow, which may optionally be reversed, as described above. Such an embodiment can be beneficial in removing or reducing the presence of bubbles on or near the surface of ultrasonic transducer 405, which can otherwise impede image quality and overall system performance.

During operation, torque cable 120, fluid conduit 110, remote housing 400, and ultrasonic transducer 405 rotate under application of an external torque, thus enabling the scanning of a spatial zone external to catheter 100. Scanning and longitudinal translation of the entire catheter 100 or the rotating elements within the catheter thus enable the collection of images over a range of intraluminal positions. The distal portion of external sheath 105 is formed from a material that permits substantial transmission of ultrasound waves through its walls. Nylon, Pebax, TPX, polyethylenes and several other compositions are examples of materials that have such a property.

FIG. 5(b) illustrates another embodiment in which transducer 405 is tiltably mounted on pivot 440, where an angular orientation of transducer 405 is selected by varying a rotational speed of torque cable 120. Such an embodiment, and related embodiments involving a fixed transducer and a deflectable, movable, or pivotable member configured to vary an imaging angle of the transducer in response to changes in the angular velocity of the imaging assembly, are disclosed in US Patent Publication No. 20080177138 (titled "Scanning Mechanisms for Imaging Probe" and filed on Jan. 22, 2008) and US Patent Publication No. 20090264768 (titled "Scanning Mechanisms for Imaging Probe" and filed on Mar. 27, 2009), both of which are incorporated by reference in their entirety. As further described in these patent publications, a restoring mechanism, such as a spring, may be included for biasing an orientation of the deflectable member in a given angular direction and/or towards a pre-selected angular orientation. A mechanical stop may also be included within the imaging assembly to limit the deflection angle of the deflectable member.

As shown in FIG. 5(b), the flow provided by working fluid to transducer 405 can be employed for exerting a torque, or restoring force, on the deflectable transducer that influences the orientation of transducer 405. FIG. 5(b) also shows how the flow path can be designed to direct the working fluid to effectively remove obstructions, such as air bubbles. It does this by directing flow to run parallel to desired surfacing, pushing the obstructions away. Fluid directing component 411 directs the flow to run parallel to the bottom face of transducer 405, and then the distal dome portion of outer sheath 105 redirects the flow to run parallel to the top face of transducer 405. The obstructions on the top face of transducer 405 impede the passage of acoustic waves, and air bubbles between transducer 405 and remote housing 400 create surface tension that impedes the deflection of transducer 405. Other features may be included to further direct flow to remove obstructions from key surfaces.

For example, in some embodiments, there may be one or more straight or curved flow passageways of various sizes and shapes to help direct flow.

FIGS. 5(c)-(e) show further embodiments in which remote housings 400 are configured to direct the flow of working fluid through channels 450 in remote housing 400. Channels 450 cause the working fluid to flow along an underside of remote housing 400 and emerge at a longitudinal position that is distal to ultrasonic transducer 405. This ensures that the working fluid does not directly impinge on ultrasonic transducer 405, thereby reducing a direct fluidic pressure applied to ultrasonic transducer 405 and having a lesser effect on its rotational dynamics and stability. Working fluid emerging from inner lumen 115 is redirected by wall 455 in remote housing, and electrical connections are made through passage 460, which is itself sealed and impervious to fluid flow. FIGS. 5(d) and 5(e) show the lateral locations of pivot holes 470 positioned on opposite sides of remote housing in order to receive pivot pins 440.

In one embodiment, a conductive coiled spring 480 lies on either side of the housing and extends from the inner surface of remote housing 400 to a lateral surface of transducer 405. The conductive coiled springs 480 may be insulated and may be connected via a straight extension of the spring material to either the signal connection 425 or ground connection 420. Each spring 480 may electrically contact transducer 405 at a lateral surface of the transducer, provided that each lateral surface of transducer 405 is connected to the active portion of the transducer such that applying a voltage across the lateral surfaces of transducer 405 results in a voltage being applied across the active portion of transducer 405. This can be achieved, for example, by providing one or more internal electrically conductive pathways within transducer 405 to achieve suitable electrical contact. Alternatively, contact points between electrically conductive pathways in the transducer and the springs 480, other than the exemplary lateral surfaces can be incorporated into the transducer to achieve the same effect.

One area where bubbles may be undesired is at springs 480 as shown in FIG. 5(d), as the bubble surface tension may interfere with the proper twisting of the springs. Suitable channels or fluidic directing structures may be provided to remove bubbles, or prevent the formation of bubbles, in or near springs 480.

FIG. 5(f) shows an embodiment of the distal portion of catheter 100 where fluid flows in a proximal to distal direction through both outer lumen 130 and inner lumen 115. Working fluid may flow through a distal flush port 135 near the distal portion 140 of catheter 100. Thus, both the inner lumen 115 and outer lumen 130 enable proximal to distal flow. The fluid may be provided to outer lumen in many ways. In one embodiment, the working fluid is in fluid communication with outer lumen 130 near fluid rotary joint 160. For example, distal seal 225 may be partially permeable to flow. In such an embodiment, secondary port 320 may not be required, or may functionally exist as port 135, as working fluid delivered to outer lumen 130 is provided by primary port 205. The amount of resistance to flow across distal seal 225 would determine the relative flow rates through the inner lumen relative to the outer lumen, with higher resistance across distal seal 225 causing higher flow rates in the inner lumen relative to the outer lumen. Higher flow rates through the inner lumen may provide more effective flushing of bubbles off of the emitting surface of acoustic transducer 405, while higher flow rates through the outer lumen may minimize effects on transducer tilting with embodiments similar to those in FIG. 5b. Alternatively, distal seal 225 can be omitted to enable flow through both the outer lumen and the inner lumen in the same direction.

While the flow of working fluid has been described, in the preceding embodiments, as flowing from primary port 205 to secondary port 320 through inner lumen 115 and outer lumen 130, it is to be understood that working fluid may alternatively be flowed in an opposite configuration in which the working fluid returns along the inner lumen 115. Such an alternative embodiment is illustrated in FIG. 5g.

FIG. 5h shows an embodiment where the fluid rotary joint is used to cool a mechanical rotary tool. The rotary tool 404 may be include tools for rotary ablation, such as a coronary atherectomy device including the Rotoblator™ and other tools with abrasive burrs for mechanical dislodging tissue under high rotational speed. Depending on the rotational speed, the environment and the tissue being dislodged, significant heat can be generated. Tool 404 contains a network of internal channels 406 through which a cooling agent may be circulated to actively cool or heat the mechanical rotary tool. Since network 406 is kept isolated from the exterior of the probe, a number of cooling agents may be used with a reduced risk of damage from exposure to bodily fluids and tissues including water, saline, gases such as nitrous oxide, and others known in the art. Network 406 may be controllably formed using machining methods, injection molding, SLA, SLS, FDM, Polyjet, and others known in the art. Furthermore, network 406 may be a chaotic network without predefined paths, such as those that may be present in porous materials such as ceramics, plastics, or metal foams.

FIG. 5i shows an example embodiment where the fluid rotary joint is interfaced with a balloon catheter, such that an expandable volume of the balloon may be increased in response to a pressure within the inner lumen of the rotatable fluid conduit. In the example embodiment shown in FIG. 5i, an optical imaging assembly 407 is connected with, or in optical communication with, optical fiber 417, and is supported within remote housing 427. This imaging assembly may be used for optical imaging using OCT, spectroscopy, angioscopy, and other optical imaging modalities known in the art. The balloon 409, once inflated, may be used to displace blood in a lumen to allow for adequate penetration of imaging energy. Fluid or gas used to inflate the balloon flows through the fluid rotary joint (not shown) to a location remote from the proximal end of the catheter and through balloon access ports 416 following example flow paths 430.

The optical imaging modality may be replaced by another imaging modality such as ultrasound. The balloon may further be used to perform a therapeutic procedure that requires the use of a therapeutic agent. For instance, the use of refrigerants such as nitrous oxide, liquid nitrogen, or liquid helium with balloon catheters to perform cryoablation of tissue has been described in the art. While the therapeutic procedure is being performed, the imaging tool may be used simultaneously to monitor and/or guide the therapy.

Referring now to FIG. 6, a system diagram is provided showing the main components of an example catheter-based system 500 employing a fluid rotary joint. System 500 includes imaging probe 544, which connects via patient interface module 536 to image processing and display system 549. Image processing and display system 549 includes hardware to support one or more imaging modalities, such as ultrasound, optical coherence tomography, angioscopy, infrared imaging, near infrared imaging, Raman spectroscopy-based imaging, or fluorescence imaging. Specific embodiments of ultrasonic imaging probes and combined ultrasonic and optical imaging probes are disclosed by Courtney et al. in US Patent Publication No. 20080177183, titled "Imaging Probe with Combined Ultrasounds and Optical Means of Imaging" and filed on Jan. 22, 2008, US Patent Publication No. 20080177138, titled "Scanning Mechanisms for Imaging Probe" and filed on Jan. 22, 2008 and US Patent Publication No. 20090264768, titled "Scanning Mechanisms for Imaging Probe" and filed on Mar. 27, 2009, each of which are incorporated herein by reference in their entirety.

Controller and processing unit 534 is employed to facilitate the coordinated activity of the many functional units of the system, and may contain some or all of the components shown in the Figure and listed herein. An operator interacts with image processing and display system 549 via display and/or user interface 538. System 500 may further include electrode sensors 540 to acquire electrocardiogram signals from the body of the patient being imaged or treated. The electrocardiogram signals may be used to time the acquisition of imaging data in situations where cardiac motion may have an impact on image quality. The electrocardiogram may also serve as a trigger for when to begin an acquisition sequence, such as when to begin changing the speed of rotation of a motor in order to cause a desired scan pattern to take effect. For example, electrocardiogram triggered initiation of an imaging sequence may enable images to be acquired during a particular phase of the cardiac cycle, such as systole or diastole.

Optical subsystem 530, if included in a particular implementation of an imaging system, may include any or all of the following components: interferometer components, one or more optical reference arms, optical multiplexors, optical demultiplexers, light sources, photodetectors, spectrometers, polarization filters, polarization controllers, timing circuitry, analog to digital converters, parallel processing arrays and other components for facilitating any of the optical imaging techniques. Ultrasound subsystem 532 may include any or all of the following components: pulse generators, electronic filters, analog to digital converters, parallel processing arrays, envelope detectors, amplifiers including time gain compensation amplifiers and other components for facilitating acoustic imaging techniques.

Controller and processing units 534, if included in a particular implementation of the imaging system, serve multiple purposes. Those skilled in the art will appreciate that specific components required depend on the needs of a particular type of imaging system. For example, controller and processing units may include any combination of a motor drive controller, data storage components (such as memory, hard drives, removable storage devices, readers and recorders for media such as CDs, DVDs, and Bluray™ discs), position sensing circuitry and/or software, angle detection circuitry and/or software, timing circuitry and/or software, cardiac gating functionality, volumetric imaging processors, scan converters and others. As noted above, display and user interface 538 is also optionally provided for either real time display or display of data at a time later than the time at which imaging data is acquired.

It is to be understood that patient interface module 536 and controller and processing units 534 are but one example illustration of the selection and organization of hardware subsystems, and that many other implementations are possible. For example, patient interface module 536 may be housed with controller and processing units 534 within processing and display system 549.

Imaging catheter 100, as described above, includes a torque cable housing a fluid conduit 110 that is connected to a fluid rotary joint 200. Catheter 100 also houses active channel 546 that includes at least one optical waveguide or a conductive path (for example, provided by two conductive wires) that connect an emitter and/or receiver via connection to an adapter, herein referred to as a patient interface module, or patient interface module 536. Active channel 546 may include a fiber optic, for example, wrapped by two layers of electrical wire that are electrically insulated from one another. Active channel 546 may further be reinforced by other structural features, such as helically wrapped wires or other designs used to construct imaging torque cables for rotating scan mechanisms.

Additional sensors may be incorporated as part of patient interface module 536, such as position sensing circuitry, for example, to sense the angle of rotation of a rotary component within the imaging probe 544 and/or for detecting the angle of deflection of a member at the distal end 541 of the imaging probe 544. Imaging probe 544 may also include a memory component such as an EEPROM or other programmable memory device that includes information regarding the imaging probe to the rest of the imaging system. For example, it may include information regarding the identification of specifications of the imaging probe 544 or may include calibration information for the imaging probe 544. Additionally, patient interface module 536 may include amplifiers to improve the transmission of electrical signals or power between the imaging probe 544 and the rest of the system.

The preceding embodiments have been illustrated using examples including ultrasonic and fiber optic imaging modalities, which can be readily employed for improved imaging systems for application such as intravascular ultrasound, optical coherence tomography, and intracardiac echocardiography, which employ rotary systems for scanning. However, it is to be understood that the systems and devices described herein are not limited to such procedures, and can be employed in a wide variety of diagnostic and therapeutic procedures. Additional example procedures include direct atherectomy, rotational atherectomy, laser ablation, and combined visualization and treatment procedures, such as image guided cryoblation, balloon angioplasty, and thrombectomy.

The aforementioned embodiments address a number of problems related to minimally invasive procedures involving scanning catheter systems. In particular, embodiments disclosed herein may support the miniaturization of catheter systems that employ an internal fluid delivery lumen with a forward and return fluidic path.

It is to be understood that fill/purge rate of the catheter may be selected by selecting an appropriate size of the fluid conduit and inner lumen. Moreover, the present embodiments have demonstrated examples in which the design is adapted for both open and closed catheter systems.

Embodiments in which the inner lumen and outer lumen form a closed fluid path eliminate the contact of biological fluids with the internal components of the catheter, and mitigate the requirements for internal sterilization. A closed system also avoids the need for pre-filling, which is associated with problems such as absorption of water by plastics, freezing, sterility, corrosion issues, and additional weight.

Conversely, open systems involving a rotatable inner conduit (that has a fluid lumen in fluid communication with a non-rotational external port), such as that in FIG. 5(f), enable the delivery of higher flush volumes in a smaller form factor, and may provide more flexibility in control of flow patterns within the catheter.

The working fluid can be employed for a wide variety of uses, including providing a medium for the coupling of imaging energy to and from imaging devices, providing internal protection and/or cleaning of internal sensor surfaces (such as optical components and ultrasound transducers), heating and/or cooling, sterilization, providing a force for scanning systems involving rotatable components. As illustrated in FIG. 5, the geometry of the distal portion of the catheter may be configured for tailoring the flow profile within the distal portion of the catheter relative to sensitive or critical locations, enabling the positioning of the active channels (e.g. fiber optic and/or electrical conductive channels) outside of the flush lumen. The diameter of the fluid conduit lumen may also be varied along its length, which can be useful, for example, in controlling the local properties such as the flow rate, pressure on selected surfaces, flow profile, and/or other properties such as the Reynolds number.

In one embodiment, a catheter or medical probe with a rotary fluid joint as described above may be employed to control the temperature of the working fluid and to expose the internal components of the catheter or medical probe to different thermal environments. For example, controlling the temperature of the working fluid can support the warming or cooling of an internal portion or device of the catheter or probe, and/or to warm or cool tissue surrounding catheter external sheath 105. In other non-limiting examples, the control of the working fluid can be employed for the a change in the shape of a memory alloy (such a nitinol) employed within catheter 100, and to cause a phase transition of a material housed within catheter 100, such as gallium or gallium-based alloys such as galistan, that undergo phase transitions at temperatures close to body temperature.

In some cases, it might be desirable to use a gas rather than a liquid within a catheter. For example, gases may be used to make a portion of the catheter more buoyant, and help direct it within a fluid filled space, such as the cardiovascular system. Furthermore, gases are generally less viscous than fluids, and may enable heat transport or inflation of balloon chambers along the length of the catheter more readily than fluids.

In another embodiment, the fluid rotary joint may be employed as part of a system that not only enables purging of air from the catheter, but also enables varying the pressure within inner lumen 115 and outer lumen 130. For example, after purging air out of the catheter using primary port 205 as an infusion port and secondary port 320 as a venting port, it may then be possible to increase the pressure within the lumens of the catheter by effectively closing one of the two ports, such as using a stopcock valve, clamp or a plug and applying pressure to the internal lumens of the catheter via the other port. Alternatively, it may be possible to decrease the pressure within the lumens of the catheter by effectively closing one of the two ports, such as using a stopcock valve, clamp or a plug and applying suction to the internal lumens of the catheter via the other port. A pressure gauge may be in fluid communication with the internal lumens of the catheter to measure the amount of pressure applied. Such pressure changes may inflate or deflate one or more balloons along the length of the catheter or actuate some other pressure-dependent mechanism.

Example embodiments provided above have been illustrated as catheter-based systems, in which a fluid rotary joint is interfaced with a rotatable fluid conduit of a catheter. However, it is to be understood that a catheter is but one example of a medical probe that may be configured according to the present disclosure. For example, in other example implementations, a medical probe may include a rotatable fluid conduit that is housed within an insertable tube such as a cannula, trocar, and/or hypodermic needle, where the rotatable fluid conduit is interfaced with a fluid rotary joint as described above.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A medical probe comprising:
    an external sheath;
    a rotatable fluid conduit housed within said external sheath, said rotatable fluid conduit including an inner lumen, wherein at least a portion of said rotatable fluid conduit is impermeable to liquids; and
    a fluid rotary joint comprising:
        an outer housing including an external port, wherein a proximal portion of said external sheath is connected to a distal region of said outer housing;
        a rotatable insert having an inner channel, wherein said rotatable insert is housed within said outer housing and rotatable within said outer housing, and wherein a proximal portion of said rotatable fluid conduit is connected to said rotatable insert, such that said inner channel is in fluid communication with said inner lumen, and such that said rotatable fluid conduit rotates in unison with said rotatable insert;
    said external sheath defining an outer lumen, wherein said inner lumen is in fluid communication with said outer lumen;
    a secondary port in fluid communication with said outer lumen;

at least one seal between said rotatable insert and an inner surface of said outer housing;
wherein said inner channel is in fluid communication with said external port under rotation of said rotatable fluid conduit; and
wherein said rotatable insert is connectable to a rotational drive mechanism.

2. The medical probe according to claim 1 further comprising a distal port formed in a distal portion of said external sheath.

3. The medical probe according to claim 1 wherein said rotatable insert comprises a longitudinal channel;
wherein said longitudinal channel is in fluid communication with said external port under rotation of said rotatable insert; and
wherein said proximal portion of said rotatable fluid conduit is received within said longitudinal channel.

4. The medical probe according to claim 3 wherein said rotatable insert comprises a lateral channel, wherein said lateral channel is in fluid communication with said longitudinal channel, and wherein said lateral channel is in fluid communication with said external port under rotation of said rotatable insert.

5. The medical probe according to claim 4 wherein said lateral channel is radially oriented.

6. The medical probe according to claim 4 wherein an outer portion of said rotatable insert includes an annular channel in fluid communication with said lateral channel and said external port.

7. The medical probe according to claim 4 wherein an inner portion of said outer housing includes an annular channel in fluid communication with said lateral channel and said external port.

8. The medical probe according to claim 1 wherein said outer housing further includes said secondary port, and wherein said outer lumen is in fluid communication with said secondary port.

9. The medical probe according to claim 1 wherein said secondary port is located near said proximal portion of said rotatable fluid conduit.

10. The medical probe according to claim 1 wherein said secondary port is located at a position that is remote from said proximal portion of said rotatable fluid conduit.

11. The medical probe according to claim 1 wherein said rotatable fluid conduit includes a torque cable.

12. The medical probe according to claim 1 further comprising:
a remote assembly connected to a rotatable portion of said medical probe at a location remote from a proximal end of said rotatable fluid conduit; and
an active channel to deliver power or signals between said proximal end of said rotatable fluid conduit and said remote assembly.

13. The medical probe according to claim 12 wherein said remote assembly includes a transducer supported by a remote housing, wherein said remote housing is attached to a rotatable portion of said medical probe.

14. The medical probe according to claim 13 wherein said transducer is an imaging transducer.

15. The medical probe according to claim 13 wherein said transducer is an ultrasonic transducer.

16. The medical probe according to claim 13 wherein said remote housing is configured to redirect a flow of working fluid delivered from said inner lumen.

17. The medical probe according to claim 16 wherein said remote housing is configured such that flow of said working fluid is directed towards a surface of said transducer.

18. The medical probe according to claim 16 wherein said remote housing is configured such that a flow of said working fluid is initially directed to a region distal to said transducer.

19. The medical probe according to claim 13 wherein said remote housing includes a flow redirecting feature to redirect a flow of working fluid.

20. The medical probe according to claim 13 wherein said remote assembly comprises a deflectable member to control a direction of imaging energy that is received with or emitted from said transducer.

21. The medical probe according to claim 20 wherein said deflectable member includes an ultrasonic transducer.

22. The medical probe according to claim 1 further comprising:
a remote device connected to a rotatable portion of said medical probe at a location remote from a proximal end of said rotatable fluid conduit;
wherein said remote device includes one or more internal flow channels in fluid communication with said inner lumen of said rotatable fluid conduit;
such that a temperature of said remote device may be controlled according to a temperature of a working fluid delivered within said rotatable fluid conduit.

* * * * *